United States Patent [19]
Higa et al.

[11] Patent Number: 5,780,441
[45] Date of Patent: Jul. 14, 1998

[54] SPHINGOGLYCOLIPID COMPOUNDS AND THERAPEUTIC USES THEREOF

[75] Inventors: Tatsuo Higa, Naha; Takenori Natori, Takasaki; Yasuhiko Koezuka, Takasaki; Kazuhiro Motoki, Takasaki, all of Japan

[73] Assignee: Kirin Beer Kabushiki Kaisha, Tokyo-To, Japan

[21] Appl. No.: 530,126

[22] PCT Filed: Apr. 14, 1994

[86] PCT No.: PCT/JP94/00625

§ 371 Date: May 7, 1996

§ 102(e) Date: May 7, 1996

[87] PCT Pub. No.: WO94/24142

PCT Pub. Date: Oct. 27, 1994

[30] Foreign Application Priority Data

Apr. 15, 1993 [JP] Japan ................... 5-088630

[51] Int. Cl.$^6$ .................. C07H 15/00; A61K 31/70
[52] U.S. Cl. .................. 514/25; 536/17.2; 536/17.9
[58] Field of Search ................... 536/17.2, 17.9; 514/25

[56] References Cited

U.S. PATENT DOCUMENTS

| | | | |
|---|---|---|---|
| 4,598,051 | 7/1986 | Papahadjopoulos | 436/512 |
| 4,728,641 | 3/1988 | Tubaro | 514/54 |
| 4,806,466 | 2/1989 | Papahadjopoulos | 435/7 |
| 4,816,450 | 3/1989 | Bell | 514/25 |
| 4,831,021 | 5/1989 | Tubaro | 514/54 |
| 4,859,769 | 8/1989 | Karlsson | 536/53 |
| 4,937,232 | 6/1990 | Bell | 514/26 |
| 4,952,683 | 8/1990 | Tschannen | 536/186 |
| 5,026,557 | 6/1991 | Estis | 424/450 |
| 5,028,715 | 7/1991 | Lyle | 548/193 |
| 5,041,441 | 8/1991 | Radin | 514/237.8 |
| 5,073,543 | 12/1991 | Marshall | 514/21 |
| 5,210,073 | 5/1993 | Yodoi | 514/12 |
| 5,567,684 | 10/1996 | Ladisch et al. | 514/25 |

FOREIGN PATENT DOCUMENTS

| | | |
|---|---|---|
| 254105 | 1/1988 | European Pat. Off. |
| 371414 | 6/1990 | European Pat. Off. |
| 0609437 | 8/1994 | European Pat. Off. |
| 61-57594 | 3/1986 | Japan . |
| 62-39597 | 2/1987 | Japan . |
| 63-45293 | 2/1988 | Japan . |
| 64-95 | 1/1989 | Japan . |
| 193562 | 4/1989 | Japan . |
| 9356289 | 4/1989 | Japan . |
| 5-9193 | 1/1993 | Japan . |
| 5-59081 | 3/1993 | Japan . |
| 2588729 | 12/1996 | Japan . |
| 9212986 | 8/1992 | WIPO . |
| 93/5055 | 3/1993 | WIPO . |
| 94/02168 | 2/1994 | WIPO . |

OTHER PUBLICATIONS

Akimoto et al. Tetrahedron Letters, vol. 34, No. 35, pp. 5593–5596, 1993.
Natori et al. Tetrahedron, vol. 50, No. 9, pp. 2771–2784, 1994.
English translation of JP application 93562/1989.
English translation of claims of Japanese patent 2588729, 1996.
Hall, Eric. J. "Radiobiology for the Radiologist" Second Ed., Ch. 1, 9 and 11, 1978. Harper & Row—Philadelphia.
Carroll, F.I., et al. J. Med. Chem., 1990, 33: 2501–2508.
Ende, N. "Life Sciences" vol. 51, pp. 1249–1253, 1992.
Motoki, K. "Radioprotective Effects . . ." Bioorganic and Medicinal Chemistry Letters, vol. 5, No. 22, pp. 2413–2416, 1995.
Higuchi, R. et al. "Structures of three New Cerebrosides . . ." Liebigs Ann Chem., 1990, 659–663.
Higuchi, R., et al. "Isolation and Characterization . . ." Liebigs. Ann. Chem. 1990, 51–55.
Stults, C.L.M. et al. Methods in Enzymology, vol. 179, Complex Carbohydrates, ed. Victor Ginsburg, vol. 179, 167–214 (1989).
Macher, B.A. Methods in Enzymology–Complex Carbohydrates, vol. L, ed. Victor Ginsburg, pp. 236–250 (1978).
Sen–itiroh HaKomori "Chemistry of Glycosphingolipids," Handbook of Lipid Research, vol. 3, ed. Julian Kanfer, pp. 1–165 (1983).
Makita, et al. "Glycosphingolipids," New Comprehensive Biochemistry, vol. 10, pp. 1–99 (1985).
Tamura, M. et al. Transplantation vol. 51, No. 6, pp. 1166–1170 Jun. 1991.

(List continued on next page.)

*Primary Examiner*—Kathleen K. Fonda
*Attorney, Agent, or Firm*—Ladas & Parry

[57] ABSTRACT

The present invention relates to a sphingoglycolipid represented by the formula (I):

wherein $R_1$, $R_2$ and $R_5$ represent H or a specific monosaccharide; $R_3$ and $R_6$ represent H or OH, respectively;

$R_4$ represents H, OH or a specific monosaccharide;

X denotes an integer from 19 to 23;

$R_7$ represents any one of the following groups (a)–(g):
  (a) $-(CH_2)_{11}-CH_3$,
  (b) $-(CH_2)_{12}-CH_3$,
  (c) $-(CH_2)_{13}-CH_3$,
  (d) $-(CH_2)_9-CH(CH_3)_2$,
  (e) $-(CH_2)_{10}-CH(CH_3)_2$,
  (f) $-(CH_2)_{11}-CH(CH_3)_2$,
  (g) $-(CH_2)_{11}-CH(CH_3)-C_2H_5$.

13 Claims, 5 Drawing Sheets

OTHER PUBLICATIONS

Atkinson, K. et al. Blood, vol. 77, No. 6, Mar. 15, 1991, pp. 1376–1382.

Nienhuis, A.W. The Journal of Clinical Investigation. vol. 8, Aug. 1987, pp. 573–577.

Monroy, R.L. Blood. vol. 70, No. 5, Nov. 1987, pp. 1696–1699.

Sheridan, W.P., et al. The Lancet, Oct. 14, 1989, pp. 891–895.

Brandt, S.J. The New England Journal of Medicine, vol. 318, Apr. 7, 1988, pp. 869–876.

Komori, T. et al. Mass Spectrometry Rev. 1985, 4, 255–293.

Kalechman, Y., et al. The Journal of Immunology. vol. 145, 1512–1517, Sep. 1, 1990.

Singh, B.N. et al. "Tegument galactosylceramides . . . " Molecular and Biochemical Parasitology, 26 (1987) 99–112.

Hannun, Y.A. "Functions of Sphingolipids . . . " Science, vol. 24–3, pp. 500–507 (1–1989).

Sato, K. et al. "High Performance Tandem . . . " Anal. Chem. 1987, 59, 1652–1659.

Kawano, Y., et al. "Isolation and Structure . . . " Liebigs Ann Chem. 1988, 19–24.

Teshima, H. Exp. Hematol. vol. 17, 1989, pp. 853–858.

Souza, L.M., et al. Science, vol. 232, pp. 61–65 Apr. 4, 1986.

Isobe, R., et al. "Biomedical and Environmental Mass Spectrometry" vol. 13, 585–594 (1986).

Tsunematsu, H. et al. Biochemical and Biophysical Research Communications, vol. 146, No. 2, 907–911 (Jul. 31, 1987).

Tanikawa, S. et al. Blood vol. 76, No. 3, Aug. 1, 1990, pp. 445–449.

Okano, A. et al. Transplantation, vol. 47, No. 4, pp. 738–740 Apr. 1989.

Kodo, H. et. al. The Lancet. Jul. 2, 1988, pp. 38–39.

Blazar, B., et. al. Blood, vol. 74, No. 6, Nov. 1, 1989, pp. 2264–2269.

Shiio, T. Jpn J. Cancer Chemother. 15(3) Mar. 1988, pp. 481–485 (In Japanese; abstract only translated).

Taguchi, T. Jpn. J. Cancer Chemother. 12(2) Feb. 1985, pp. 366–378 (In Japanese; abstract only translated).

Koike, et al. Carbohydrate Research, vol. 162, No. 2, pp. 237–246, May 1, 1987.

Costello, et al. ACS Symposium Series: Cell Surface Glycolipids, vol. 128, pp. 35–54, 1980.

Uchida, et al; J. Biochem. 87:1843–1849 (1980).

Hirsch, S., et al., "New Glycosphingolipids from Marine Organisms." Tetrahedron, vol. 45, No. 12, (1989), pp. 3897–3906.

Yu, Robert K. et al. Structure and Localization of Gangliosides. Neurobiology of Gycoconjugates, ed. by Richard U. Margolis, pp. 1–42 (1989).

Sweeley, et al. "Chemistry of Mammalian Glycolipids." The Glycoconjugates, vol. 1, pp. 459–540 (1977).

Sweeley, Charles, C. "Sphingolipids." New Comprehensive Biochemistry, vol. 20, ed. Dennis E. Vance, 327–361 (1991).

Nishizuka, Y. Science 233, 305–312 (Jul. 18, 1986).

Kaibuchi, K. et al. J. Biol. Chem. 260:1366–1369 (Feb. 10, 1985).

Crabtree, G.R. Science, 243:355–361 (Jan. 1989).

Wepsic, T.H. Immunopharmacology and Immunotoxicology, vol. 11, 81–99 (1989).

Dillman, R.O. "Phase I . . . " Mol. Biother., Sep. 1992, vol. 4, 117–121.

Dyatlovitskaya, et al. Biokhimiya, 49(3), 1984, pp. 432–436, including English Abstract.

R.J. Robb, The Journal of Immunology, vol. 136, 971–976 (Feb. 1, 1986).

E.G. Bremer, The Journal of Biological Chemistry, 261, 2434–2440 (Feb. 15, 1986).

Inokuchi, et al. Cancer Letters, 38:23–30 (1987).

Radin, et al. Biochemical Pharmacology 37(15):2879–2886 (1988).

Zubay, G. "Biochemistry", pp. 527–535, 1983, Addison-–Wesley Publishing Co.

Kalisiak et al. Int. J. Cancer 49:837–845 (1991).

Wiegand, et al. Chemical Abstracts 114:122965m (1991).

K. Munesada, et al. Chem. Soc. Perkin Trans. 1991, pp. 189–194.

M. Honda, Chem. Pharm. Bull. 39(6) 1385–1391, Jun. 1991.

Natori et al. *Tetrahedron Letters* 1993, 34(35), 5592–5593.

Koike et al. *Agric. Biol. Chem.* 1990, 54(3), 663–667.

Higuchi, R. et al. "Structure and Biological Activity of Ganglioside Molecular Species". Liebigs Annalen der Chemie, vol. 1993, No. 4, Apr. 1993, pp. 359–366.

Sugiyama, S., et al. "Biologically Active Glycosides . . . " Liebigs Annalen der Chemie; 1991, No. 4, pp. 349–356; (04.0491).

Schmidt, R.R., et al. "Synthesis of D–ribo–and L–lyxo–phytosphingosine". . . Carbohydrate Research; vol. 174, (1988) pp. 169–179.

COMPOUND 1

COMPOUND 2

COMPOUND 3

COMPOUND 4

COMPOUND 5

COMPOUND 6

COMPOUND 7

COMPOUND 8

COMPOUND 9

COMPOUND 10

COMPOUND 11

COMPOUND 12

COMPOUND 13

COMPOUND 14

COMPOUND 15

COMPOUND 16

COMPOUND 17

COMPOUND 31

COMPOUND 33

COMPOUND 35

5,780,441

SPHINGOGLYCOLIPID COMPOUNDS AND THERAPEUTIC USES THEREOF

This is the U.S. national stage entry under 35 U.S.C. 371 of PCT/JP94/00625, filed Apr. 14, 1994.

FIELD OF THE INVENTION

The present invention relates to a novel sphingoglycolipid having a strong anti-tumor activity, a bone marrow cell-proliferation-promoting activity and an immunostimulatory activity and a use thereof. More particularly, the present invention relates to a novel sphingoglycolipid which can be used as an anti-tumor agent, a bone marrow cell-proliferation-promoting agent as well as an immunostimulating agent in the pharmaceutical field and has an improved solubility during its dissolution, and to a sphingoglycolipid-containing pharmaceutical composition, anti-tumor agent, bone marrow cell-proliferation-promoting agent as well as immunostimulating agent.

BACKGROUND OF THE INVENTION

Sphingoglycolipids have been described in Japanese Patent Laid-Open Publication Nos. 93562/1989, 59081/1993 and 9193/1993, and WO 93/05055, and particularly the sphingoglycolipid described in WO 93/05055 is a compound having a distinguished anti-tumor activity and immunostimulatory activity.

These compounds are however the cerebrosides having a ceramide portion to which a monosaccharide is linked and thus have an extremely poor solubility in water. For instance, the clinical application of the compounds as injection requires a pharmaceutically acceptable adjuvant such as surface active agent for suspending or dissolving them into water. And, Polysorvates (Tweens) may be used as a surface active agent. However, such a surfactant has been reported to have a vasostimulant effect on its intravascular administration and to exhibit the increased cardiac output and the decreased peripheral vascular resistance when administered to human subjects (Journal of the Amerikan College of Toxicology, Vol. 3, No. 5, 1–82 (1984)). Such symptoms are considered as the adverse effects of the Polysorbate administered in a high concentration as a dissolving aid. Moreover, while the compound of the present invention is aimed at its use as an anti-tumor agent, bone marrow cell-proliferation-promoting agent as well as immunostimulating agent, Polysorbate is described to have a primary antibody-reaction-suppressing effect on immune systems by Bryant R. L. et al., Arch. Allergy Appl. Immunol., Vol. 59, 69–74 (1979), and an effect of promoting the metastasis of cancer by Kiricuta I., et al., Rev. Roum. Embryol. Cytol. Ser. Cytol., Vol. 8, 29–32, (1971), so that it exhibit an effect quite adverse to the intended use of the compound according to the present invention.

In addition, polyethylene glycol which is known as another dissolving aid has been described to have adverse effects including lactic acidosis, lake, cardiac dysrhythmia and the like by Speth, P. A. J., et al., Therapeutic Drug Monitoring, Vol. 9, 255–258 (1987), and dimethylformamide and dimethylacetamide has also been described to cause hepatic disorders by Gerald, L., et al., Drug and Chemical Toxicology, Vol. 9, 147–170 (1988).

Adverse effects of only a few dissolving aids have been described above, and the other dissolving aids are also known to have adverse effects.

It is therefore essential to decrease as much as possible the amount a surface active agent such as Polysorbate in order to ensure the safety of patients in the clinical application of a sphingoglycolipid and to use the pharmaceuticals more effectively. It can be considered desirable from this viewpoint to enhance the solubility of a sphingoglycolipid in water for its clinical application.

Furthermore, insofar as we know, neither one of the compounds described above have been reported to be practically employed as an anti-tumor agent, a bone marrow cell-proliferation-promoting agent as well as an immunostimulating agent. In addition, the physiological activity of a chemical substance depends primarily on its chemical structure, so that it is always demanded to have a novel compound having an anti-tumor activity, a bone marrow cell-proliferation-promoting activity and an immunostimulating activity.

DISCLOSURE OF THE INVENTION

The object of the present invention is to provide a novel compound which has an increased and improved solubility in water and can be practucally employed as an anti-tumor agent, a bone marrow cell-proliferation-promoting agent as well as an immunostimulating agent.

The present inventors have found that a sphingoglycolipid having an specific chemical structure exhibits an anti-tumor activity, a bone marrow cell-proliferation-promoting activity and an immunostimulating activity, that the compound has a solubility in water superior to that of conventional cerebrosides, and that analogues of the compound synthesized have also the similar activities. Thus, the present invention has been accomplished on the basis of these findings.

That is, the sphingoglycolipid according to the present invention is the compound represented by the formula (I):

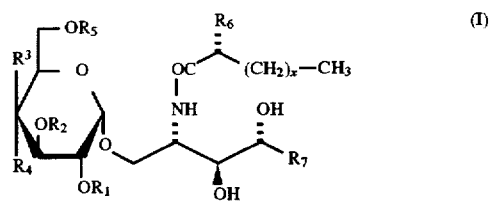

wherein $R_1$ represents H or

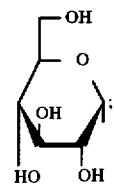

$R_2$ represents H,

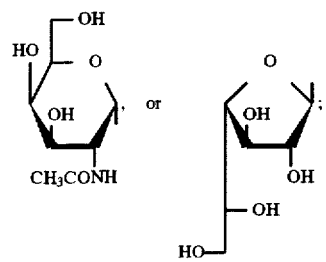

$R_3$ and $R_6$ represent H or OH, respectively;

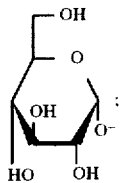

$R_4$ represents H, OH, or

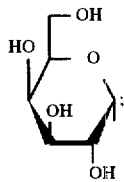

$R_5$ represents H or

X denotes an integer from 19 to 23;

$R_7$ represents any one of the following groups (a)–(g):
(a) —$(CH_2)_{11}$—$CH_3$,
(b) —$(CH_2)_{12}$—$CH_3$,
(c) —$(CH_2)_{13}$—$CH_3$,
(d) —$(CH_2)_9$—$CH(CH_3)_2$,
(e) —$(CH_2)_{10}$—$CH(CH_3)_2$,
(f) —$(CH_2)_{11}$—$CH(CH_3)_2$,
(g) —$(CH_2)_{11}$—$CH(CH_3)$—$C_2H_5$.

The present invention also relates to the use of the compound represented by the formula (I), particularly to the pharmaceutical composition, and the anti-tumor agent, the bone marrow cell-proliferation-promoting agent as well as the immunostimulating agent.

That is to say, the pharmaceutical composition according to the present invention contains the sphingoglycolipid represented by the formula (I) as an effective ingredient.

Furthermore, the anti-tumor agent, the bone marrow cell-proliferation-promoting agent as well as the immunostimulating agent according to the present invention contain the sphingoglycolipid represented by the formula (I) as an effective ingredient.

In addition, the present invention relates to a process of therapy in which an effective amount of the above-described compound is administered to a patient who require the suppression of tumor, the stimulation of proliferation of bone marrow cells or the activation of the immune system.

BEST MODE FOR CARRYING OUT THE INVENTION

Sphingoglycolipid

The sphingoglycolipid according to the present invention is represented by the formula (I) as described above, and the structures of linkage form in the sugar portion can be classified into (1)–(5) as follows:

(1) $GalNAc_p\alpha1 \rightarrow 3Gal_p(2 \leftarrow 1\alpha Glc_p)\alpha1 \rightarrow 1Cer$.
(2) $Gal_p\beta1 \rightarrow 3Gal_p\alpha1 \rightarrow 1Cer$.
(3) $Gal_p\alpha1 \rightarrow 6Glc_p\alpha1 \rightarrow 1Cer$.
(4) $Gal_p\alpha1 \rightarrow 6Gal_p\alpha1 \rightarrow 1Cer$, and
(5) $Glc_p\alpha1 \rightarrow 4Glc_p\alpha1 \rightarrow 1Cer$.

In addition, the preferred embodiments of the compound of the present invention include the sphingoglycolipids represented by the formulae (II) and (III):

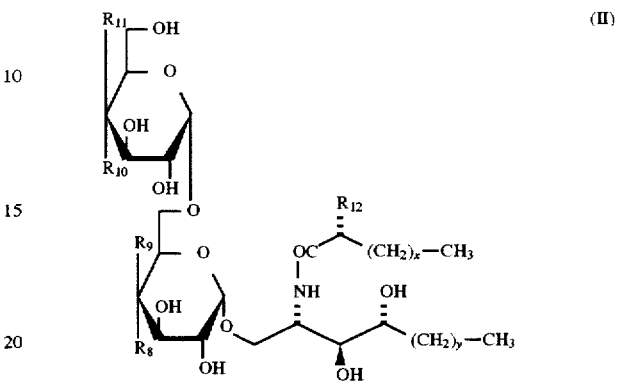

wherein if $R_8$ represents OH, $R_9$ represents H, and if $R_8$ represents H, $R_9$ represents OH, if $R_{10}$ represents OH, $R_{11}$ represents H, and if $R_{10}$ represents H, $R_{11}$ represents OH, $R_{12}$ represents H or OH, X denotes an integer from 19 to 23, and Y denotes an integer from 11 to 13;

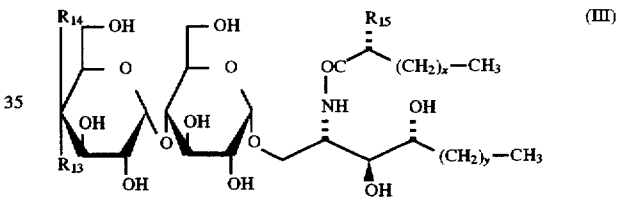

wherein if $R_{13}$ represents OH, $R_{14}$ represents H, and if $R_{13}$ represents H, $R_{14}$ represents OH, $R_{15}$ represents H or OH, X denotes an integer from 19 to 23, and Y denotes an integer from 11 to 13.

The more preferred embodiments of the present invention include the compound represented by the formula (I) wherein $R_1$, $R_2$ and $R_6$ represent H, $R_3$ represents H or OH, either one of $R_4$ and $R_5$ represent the sugar defined above, and $R_7$ represents any one of the groups (a)–(c).

Figure 1A:
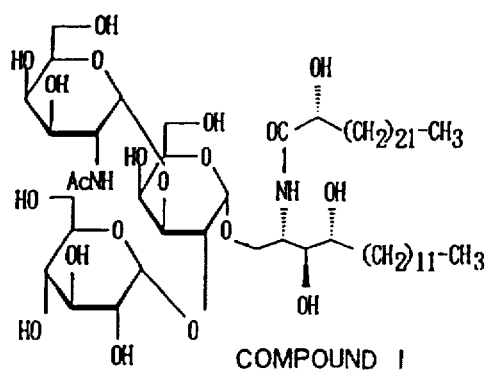
FIGS. 1a–1c illustrate schematically the chemical structures of the preferred specific compounds of the sphingoglycolipid according to the present invention.
Figure 1A:
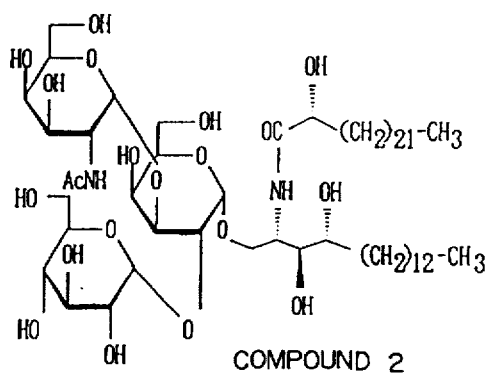
Figure 1A:
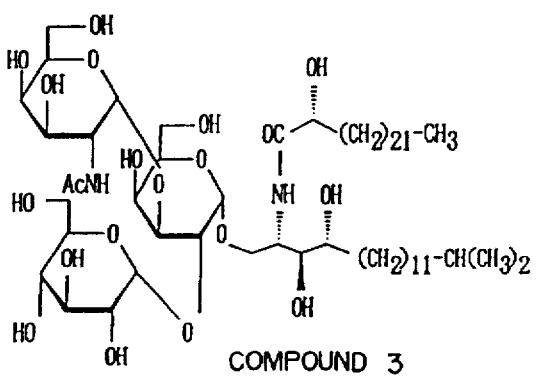
Figure 1A:
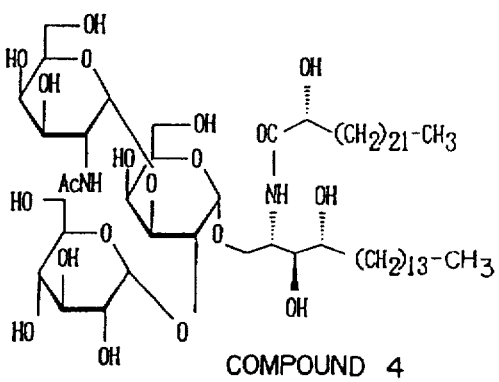
Figure 1A:
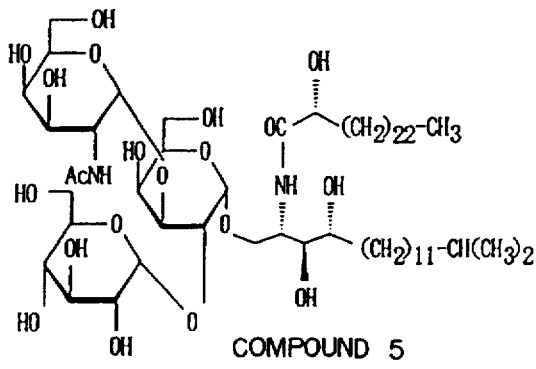
Figure 1A:
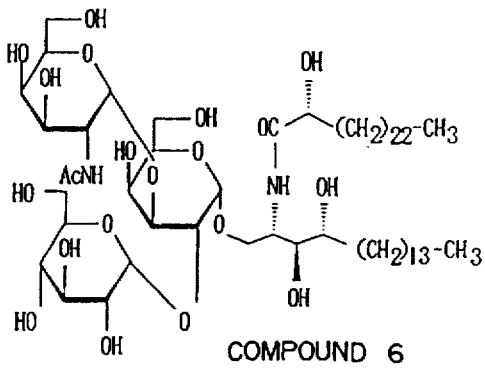
Figure 1A:
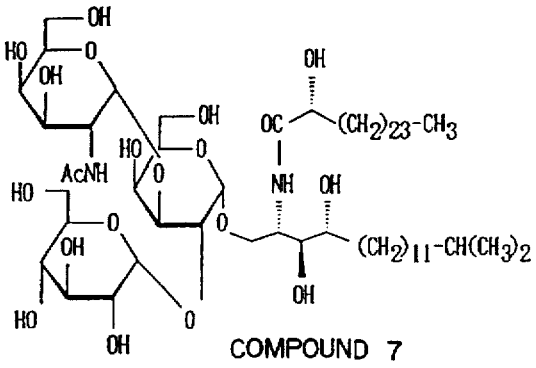
Figure 1A:
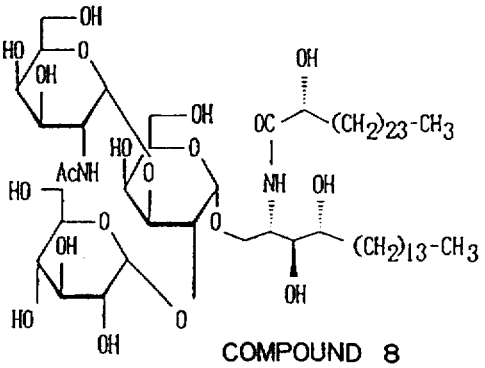
Figure 1B:
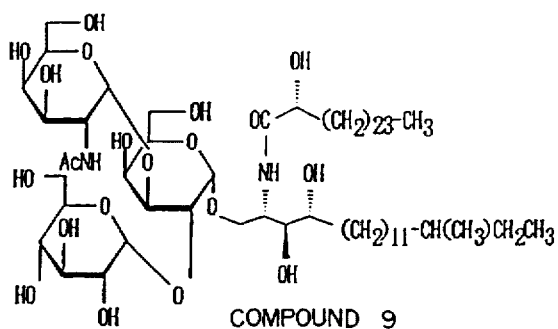
Figure 1B:
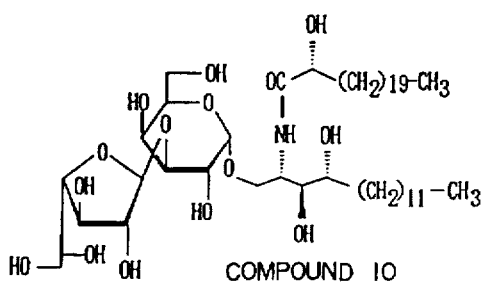
Figure 1B:
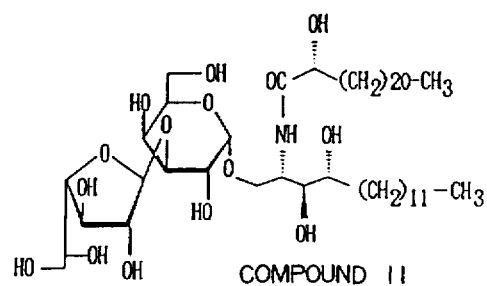
Figure 1B:
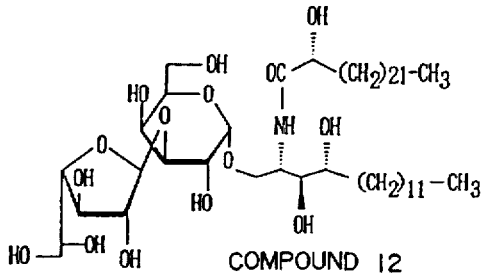
Figure 1B:
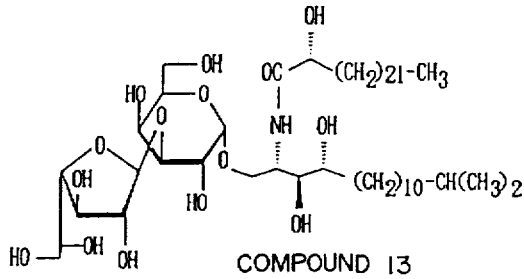
Figure 1B:
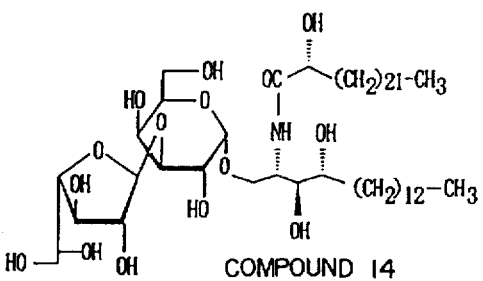
Figure 1B:
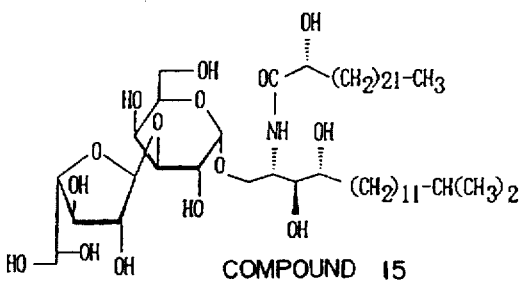
Figure 1B:
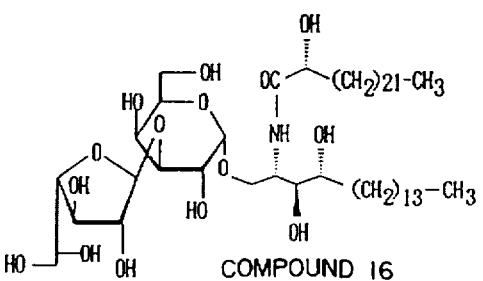
Figure 1B:
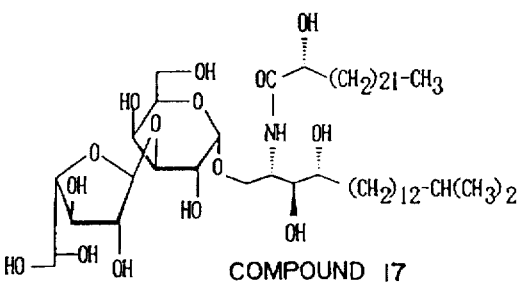
Figure 1C:
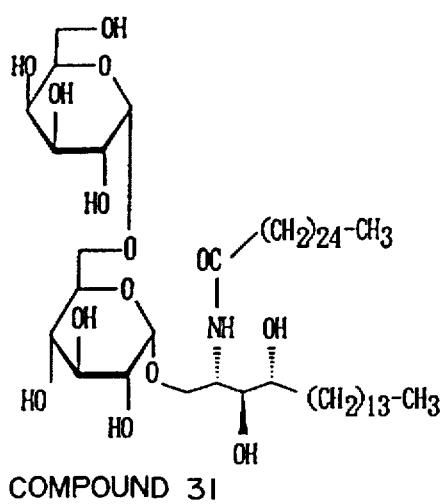
Figure 1C:
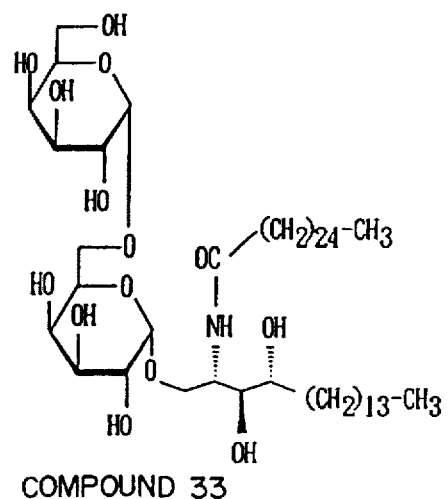
Figure 1C:
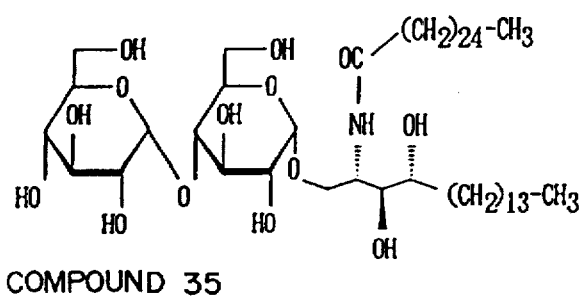

The embodiements of the sphingoglycolipids of the present invention represented by the formula (I) preferably include the following compounds 1–17, 31, 33 and 35, more preferably the compounds 31, 33 and 35 (the structural formulae of these compounds are illustrated in FIGS. 1a–1c).

Compound 1: O-(N-acetyl-2-amino-2-deoxy-α-D-galactopyranosyl)-(1→3)-O-[α-D-glucopyranosyl-(1→2)]-O-α-D-galactopyranosyl-(1→1)-(2S,3S,4R)-2-amino-N-[(R)-2-hydroxytetracosanoyl]-1,3,4-hexadecanetriol;

Compound 2: O-(N-acetyl-2-amino-2-deoxy-α-D-galactopyranosyl)-(1→3)-O-[α-D-glucopyranosyl-(1→2)]-O-α-D-galactopyranosyl-(1→1)-(2S,3S,4R)-2-amino-N-[(R)-2-hydroxytetracosanoyl]-1,3,4-heptadecanetriol;

Compound 3: O-(N-acetyl-2-amino-2-deoxy-α-D-galactopyranosyl)-(1→3)-O-[α-D-glucopyranosyl-(1→2)]-O-α-D-galactopyranosyl-(1→1)-(2S,3S,4R)-2-amino-N-[(R)-2-hydroxytetracosanoyl]-16-methyl-1,3,4- heptadecanetriol;

Compound 4: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-1,3,4-octadecanetriol;

Compound 5: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-16-methyl-1,3,4-heptadecanetriol;

Compound 6: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|- 1,3,4-octadecanetriol;

Compound 7: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-16-methyl-1,3,4-heptadecanetriol;

Compound 8: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-1,3,4-octadecanetriol;

Compound 9: O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-16-methyl-1,3,4-octadecanetriol;

Compound 10: O-β-D-galactofuranosyl-(1→3)-O-α-D-galactopyranosyl-(1→1)-(2S,3S,4R)-2-amino-N-|(R)-2-hydroxydocosanoyl|-1,3,4-hexadecanetriol;

Compound 11: O-β-D-galactofuranosyl-(1→3)-O-α-D-galactopyranosyl-(1→1)-(2S,3S,4R)-2-amino-N-|(R)-2-hydroxytricosanoyl|-1,3,4-hexadecanetriol;

Compound 12: O-β-D-galactofuranosyl-(1→3)-O-α-D-galactopyranosyl-(1→1)-(2S,3S,4R)-2-amino-N-|(R)-2-hydroxytetracosanoyl|-1,3,4-hexadecanetriol;

Compound 13: O-β-D-galactofuranosyl-(1→3)-O-α-D-galactopyranosyl-(1→1)-(2S,3S,4R)-2-amino-N-|(R)-2-hydroxytetracosanoyl|-15-methyl-1,3,4-hexadecanetriol;

Compound 14: O-β-D-galactofuranosyl-(1→3)-O-α-D-galactopyranosyl-(1→1)-(2S,3S,4R)-2-amino-N-|(R)-2-hydroxytetracosanoyl|-1,3,4-heptadecanetriol;

Compound 15: O-β-D-galactofuranosyl-(1→3)-O-α-D-galactopyranosyl-(1→1)-(2S,3S,4R)-2-amino-N-|(R)-2-hydroxytetracosanoyl|-16-methyl-1,3,4-heptadecanetriol;

Compound 16: O-β-D-galactofuranosyl-(1→3)-O-α-D-galactopyranosyl-(1→1)-(2S,3S,4R)-2-amino-N-[(R)-2-hydroxytetracosanoyl|-1,3,4-octadecanetriol;

Compound 17: O-β-D-galactofuranosyl-(1→3)-O-α-D-galactopyranosyl-(1→1)-(2S,3S,4R)-2-amino-N-[(R)-2-hydroxytetracosanoyl|-17-methyl-1,3,4-octadecanetriol;

Compound 31: O-α-D-galactopyranosyl-(1→6)-O-α-D-glucopyranosyl-(1→1)-(2S,3S,4R)-2-amino-N-hexacosanoyl-1,3,4-octadecanetriol;

Compound 33: O-α-D-galactopyranosyl-(1→6)-O-α-D-galactopyranosyl-(1→1)-(2S,3S,4R)-2-amino-N-hexacosanoyl-1,3,4-octadecanetriol;

Compound 35: O-α-D-glucopyranosyl-(1→4)-O-α-D-glucopyranosyl-(1→1)-(2S,3S,4R)-2-amino-N-hexacosanoyl-1,3,4-octadecanetriol.

Process for Preparing the Compound of the Present Invention

The compound according to the present invention, that is the sphingoglycolipid represented by the formula (I) may be obtained by the chemical modification of the related compounds, the chemical synthetic method as the combination of a variety of general chemical reactions required for the synthesis of a sphingoglycolipid or the extraction from sponges.

i) Chemical synthetic method

As the chemical synthetic method for obtaining the sphingoglycolipid of the present invention, any appropriate methods can be used, and thus the method described in Agricultural and Biological Chemistry, 54 (3), 663, 1990 may be applied.

The sphingoglycolipid represented by the formula (I) can be synthesized by applying such preferred synthetic methods as those described in Japanese Patent Laid-Open Publication No. 9193/1993 or described in FIGS. 1–4 in WO 93/05055 (PCT/JP92/00561).

Figure 2A:
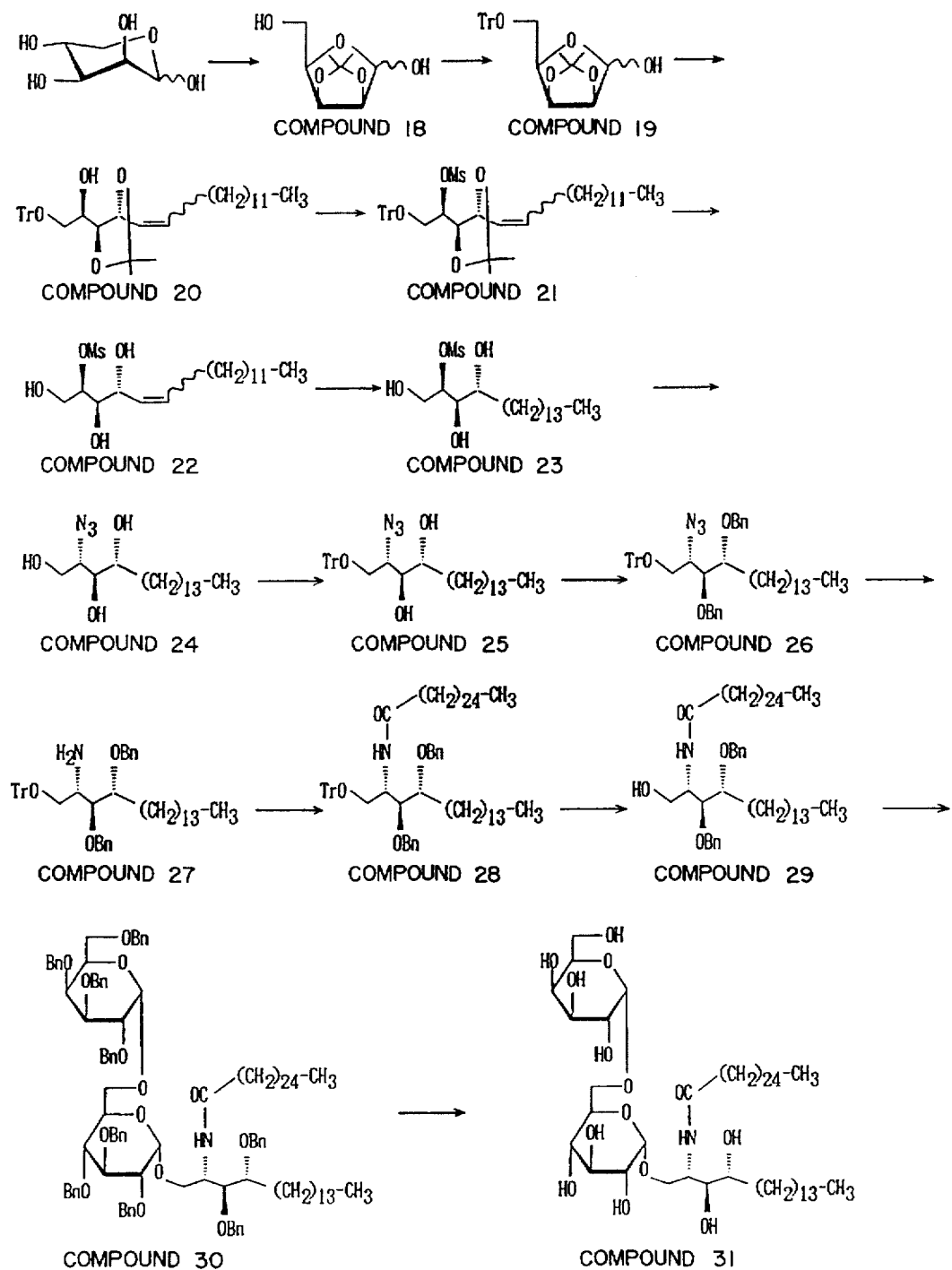
FIGS. 2a and 2b illustrates the preferred reaction scheme for synthesizing the compound represented by the formula (I) starting from a saccharide (lyxose).
Figure 2B:
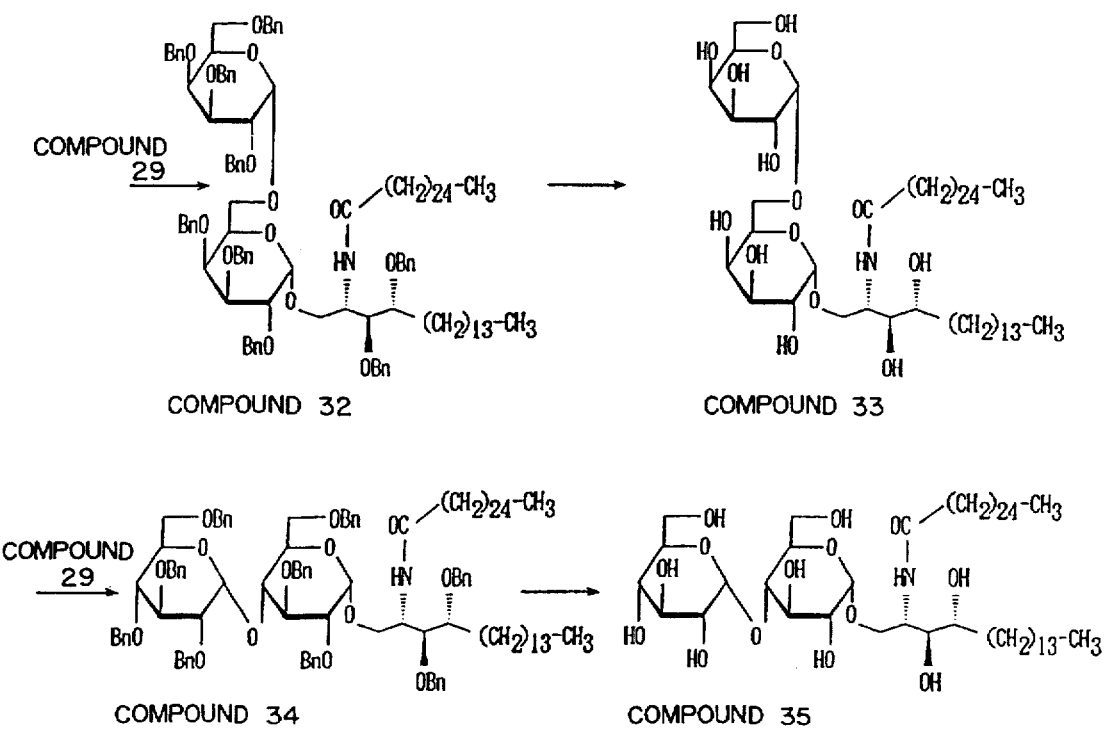

The sphingoglycolipid of the present invention can be specifically prepared for example by the total synthetic method following to the reaction scheme shown in FIGS. 2a and 2b. While the reaction scheme is illustrated on the specific compounds of the present invention (Compounds 31, 33, and 35), it can be also applied to the synthesis of the other compounds represented by the formula (I).

This method uses a saccharide as a starting material and thus can be performed in accordance to the method described in Liebigs Annalen der Chemie, 663 (1988).

The method illustrated in the reaction scheme, the details of which will be described in experimental examples below, can be described briefly as follows. In this connection, the following abbreviations are used in the reaction scheme. Bn: benzyl, Tr: trityl, Ms: methanesulfonyl.

In the method illustrated in the reaction scheme, the aimed sphingoglycolipids of the present invention (Compounds 31, 33, and 35) can be prepared by protecting a sugar (D-lyxose) as a starting material, combining with a hydrocarbon compound having 5 less carbon atoms than those in the long chain portion of a sphingosine to form Compound 20, which after an appropriate protection is linked with the carboxylic acid portion of the ceramide through azidation, reduction and amidation to form the ceramide portion (Compound 29), which is linked with the corresponding sugar by glycosylation and finally subjected to deprotection.

As the sugar as the raw material, D-galactose in addition to D-lyxose can be used. An amino acid such as L-serine can also be used in place of the sugars as the starting material.

In the reaction route described above, the reactions such as the protection of the hydroxyl group, the linking of the hydrocarbon compound to the sugar compound, azidation, amidation, and glycosylation may be carried out according to the conventional methods.

In the above example, a benzyl group and a triphenylmethyl group are used as the protective group of the hydroxyl group, but any appropriate protective groups such as a benzoyl group can also be used.

In the reaction scheme, many reaction routes have been described on amidation, and an acid chloride or an acid anhydride can be used in place of the carboxylic acid.

The reaction with the carboxylic acid is a condensation reaction in the presence of an appropriate condensation agent. The condensation agent used herein includes preferably dicyclohexylcarbodiimide (DCC), 2-ethoxy-1-ethoxycarbonyl-1,2-dihydroquinoline (EEDQ), 1-ethyl-3-(3-dimethylaminopropyl)-carbodiimide (WSC), a chlorocarbonate ester, an onium salt. An organic base such as triethylamine, pyridine, N-methylmorpholine, dimethylaniline, 4-dimethylaminopyridine, N-methylpiperidine or N-methylpyrrolidine is added in order to progress the reaction quickly. The solvent may be any inert solvent which is not involved in the reaction.

The reaction with the acid chloride conveniently proceeds generally in the presence of a solvent. The reaction is generally carried out with an appropriate solvent. In the case of a low reaction rate, quick reaction can be realized by conducting it in the absence of solvent. The solvent may be any inert solvent which will not involved in the reaction. When the reaction rate is low, quick reaction may be realized by adding an organic base such as triethylamine, pyridine, N-methylmorpholine, dimethylaniline or 4-dimethylaminopyridine.

The reaction with an acid anhydride is preferably carried out in the presence of an appropriate base. The base used herein includes triethylamine, pyridine and the like, which generally serve also as the solvent.

Also, as to glycosylation, there have been described many reaction methods such as those described in the reviews in ORGANIC SYNTHETIC CHEMISTRY, 38 (5), 473 (1980) and 41 (8), 701 (1983); Pure and Applied Chemistry, 61 (7), 1257 (1989); and Pharmacia, 27 (1), 50 (1991), and any one of these methods can be used in the preparation of the compound of the present invention.

In the glycosylation during the preparation of the compound of the present invention having a trisaccharide portion, the corresponding trisaccharide may be subjected to reaction in place of the disaccharide in the above reaction route. As the oligosaccharides used in the glycosylation, the commercially available ones or those obtained by the conventional method for preparing an oligosaccharide starting from a monosaccharide or a polysaccharide may be used.

While the ceramide is linked with a saccharide before the removal of the protective group in the synthetic method described above, it is also possible to accomplish the formation of a cerebroside by first linking a sugar with a long chain base as described in Liebigs Annalen der Chemie, 669, 1988 before amidation with an amino group.

As described above, synthesis of specific compounds of the present invention (Compounds 31, 33 and 35) are illustrated in the reaction scheme in FIG. 2, the other compounds represented by the formula (I) can be also prepared in accordance with the method. ii) Preparation from sponges The method of the compound of the present invention basically comprises a collection step of sponges, an extraction step and a purification step. The preferred examples of the sponges in the collection step include Stylissa fulabelliformis or Agelas axisera, which can be collected in the sea for example around Miyako-jima island, Okinawa or Amami-oshima island, Kagoshima.

In the extraction step, a technique conventionally used for extracting a sphingoglycolipid, preferably extraction with an organic solvent such as methanol, preferably a mixed solvent of methanol and dichloromethane can be used. Also, in the purification step, techniques conventionally used for purifying sphingoglycolipids such as various fractionation methods for example with use of the difference of solubilities or the difference of partition coefficients can be used appropriately. The preferred examples of these methods have been specifically described in detail in Japanese Patent Laid-Open Publication No. 9193/1993 and WO 93/05055 (PCT/JP92/00561).

Uses of the Compound of the Present Invention

The compounds of the present invention represented by the formula (I) is useful in the point that it has physiological activities such as an anti-tumor activity, a bone marrow cell-proliferation-promoting activity and an immunostimulating activity. It is useful also in the point that these physiological activities are superior to those of the conventional carcinostatic agents acting on the immune system such as lentinan which is an anti-tumor polysaccharide extracted from the fruit body of *Lentinous edodes*, referred to hereinafter as "lentinan", schizophyllan which is a polysaccharide extracted from the mycelium of *Schizophyrum commune* Fr., referred to hereinafter as "Sizofilan", and picibanil which is a lyophilized powder of the penicillin-treated Su strain of Streptococcus pyogenes ($A_3$) (Chugai Pharmaceutical Co., Ltd.), referred to hereinafter as "picibanil". Furthermore, it is also useful for preparing pharmaceutical preparations, since it exhibits an anti-tumor activity, a bone marrow cell-proliferation-promoting activity and an immunostimulating activity similar to those of the sphingoglycolipids described in Japanese Patent Laid-Open Publication No. 9193/1993 and WO 93/05055, and it exhibits a solubility in water far higher as compared with the above-described sphingoglycolipids which have been designed to have these physiological activities.

1) Anti-tumor activity

The compound according to the present invention exhibited an anti-tumor activity against mice subcutaneously inoculated with P388 mouse leukemia cells or B16 mouse melanoma cells, as shown in Experimental Example 4 below.

2) Bone marrow cell-proliferation-promoting activity

The compound according to the present invention exhibited a mouse bone marrow cell-proliferation-promoting activity in vitro as shown in Experimental Example 5 below.

3) Immunostimulating effect

The compound according to the present invention exhibited in vitro lymphocytic proliferation-stimulating effect on murine spleen cells and on murine mixed lymphocyte culture reaction (MLR) as shown in Experimental Example 6 below.

4) Radioprotective effect

The compound according to the present invention exhibited an radioprotective effect on mice which had been irradiated with lethal dose of radiation as shown in Example 7 below. Such an effect indicates indirectly the bone marrow cell-proliferation-promoting activity described above.

5) Improvement of solubility in water

The compound according to the present invention made it possible to decrease the amount of a surface active agent required for dissolving it in water to a proportion of 1/100 as compared with the amount of the surface active agent required for a compound comprising the same ceramide portion as that of the present compound in which the sugar portion was a monosaccharide as shown in Experimental Example 9 below.

6) Influence of Polysorbate on immunostimulating activity

It was indicated that the high concentrations of Polysorbate 20 suppressed the proliferation of mouse splenocytes as well as the immunostimulating activity of the compound of the present invention, but the reduced amount of Polysorbate 20 resulted in the recovery of the immunostimulating activity.

In Experimental Examples 4, 5 and 8 referred to in the above paragraph 1), 2) and 5), the compounds represented by the formulae disclosed in Japanese Patent Laid-Open Publication No. 9193/1993 and WO 93/05055, (2S,3S,4R)-1-(α-D-galactopyranosyloxy)-2-|(R)-2-hydroxytetracosanoylamino|-3,4-heptadecanediol, which is referred to hereinafter as Compound a, and (2S,3S,4R)-1-(α-D-galactopyranosyloxy)-2-hexacosanoylamino|-3,4-octa-decanediol, which is referred to hereinafter as Compound b, were used as control compounds.

7) Anti-tuor agent, bone marrow cell-proliferation-promoting agent and immunostimulating agent As described above, the compound of the present invention was found to have an excellent anti-tumor activity, bone marrow cell-proliferation-promoting activity and immunostimulating activity. Thus the compound of the present invention can be used as an anti-tumor agent (for the treatment of a solid carcinoma such as melanoma and blood carcinoma such as leukemia), a bone marrow cell-proliferation-promoting agent (for the treatment of hypocytosis due to immune disorders or to side-effects in the chemotherapy or radiotherapy of carcinoma), and an immunostimulating agent (for the treatment of a variety of carcinomas, infections and aquired immuno-deficiency syndrome). The compound of the present invention can be administered through any appropriate dosage routes and in a dosage form which is determined depending on the dosage route adopted. The pharmaceutical preparation is generally in the form diluted with a pharmaceutically acceptable carrier or diluent.

When the compound of the present invention is used as an anti-tumor agent, a bone marrow cell-proliferation-promoting agent, or an immunostimulating agent, it can be administered orally or parenterally to humans or mammalians. For instance, the compound of the present invention may be dissolved or suspended in an appropriate solvent (such as distilled water for injection) in order to inject it intravenously, intramuscularly or subcutaneously. In addition, it may be blended with an appropriate carrier or diluent which is any one of the compounds generally used for this object such as starch, sucrose, lactose or calcium carbonate, or a lubricant which is any one of the compounds generally used for this object such as stearic acid, sodium benzoate, boric acid, silica or polyethylene glycol in order to administer it orally in the form of powder, tablets, granules, capsules, troches, dry syrup and the like.

The dose of the compound of the present invention is determined in view of the results of animal tests and individual situations so that the total dose will not exceed the predetermined amount on continuous or intermittent administration. Specific doses naturally depend on dosage methods, the situations of patients or animal subjects such as ages, weights, sexes, sensitivities, feeds, administration intervals, drugs used in combination therewith, severities of subjects or diseases, and the optimum dose and dosage number under the certain condition should be determined by the specialist's test for determining the optimum dose on the basis of the above guideline.

The compound represented by the formula (I) exhibits an anti-tumor effect, a bone marrow cell-proliferation-promoting effect and an immunostimulating effect, and thus is a pharmaceutical which is classified into Biological Response Modifiers (BRMs) as described by Oldham, R. K., Natl. Cancer Inst., 70, 789–796 (1983). The dose of the compound of the present invention to human subjects were thus estimated on the basis of the doses of lentinan and schizophyllan which were the commercially available BRMs in Japan. The doses of lentinan and schizophyllan to mice and humans are shown in the following table from the result of referential examination.

|  | Dose to mice | Dose to human subjects |
| --- | --- | --- |
| Lentinan | 1–2 mg/kg[1] | 1–2 mg/body[2] |
| Sizofilan | 10–50 mg/kg[3] | 40 mg/body[4] |

[1] Taguchi, T., et al., Biotherapy, 2, 509–521 (1988),
[2] Ochiai, T., et al., Biotherapy, 3, 1375–1378 (1989),
[3] Furue, H., Medical Immunology, 12, 65–77 (1986),
[4] Furue, H., et al., Jpn. J. Cancer Chemother., 12, It was thus found out that if the dose to mice was A mg, the dose to human subjects were A mg/body. According to this case, the compound of the present invention exhibits a significant anti-tumor activity on mice on its intravenous administration at a dose of 0.1 mg/kg, so that the dose to human subjects by intravenous injection is estimated to be about 0.1 mg/body. It is however very difficult to determine the dose of BRM to human subjects, and it is necessary to perform its trial administration with a variety of doses ranging from an extremely low dose to the maximum tolerable dose (MTD) (Oldham, R. K., J. Biol. Response Mod., Vol. 4, 117–128 (1985)). Thus, the practical dose should be determined by the cautious discretion of specialists.

The present invention is now specifically described in detail with reference to experimental examples without limiting the invention thereto.

EXPERIMENTAL EXAMPLE 1: PREPARATION

A sponge Stylissa fulabelliformis in an amount of 2.0 kg collected in the sea around Miyako-jima island, Okanawa was homogenized and lyophilized (420.3 g). The product was extracted sequentially with chloroform-methanol (1:1), methanol and hot methanol in an amount of 1 liter, respectively, for 24 hours, and the extracts were combined together and evaporated to dryness under reduced pressure to give a brown extract (59.09 g). The extract was partitioned into 2 liters of water and 1 liter of chloroform, the aqueous layer being extracted thrice with 1 liter of n-butanol, which was combined with the chloroform layer and evaporated to dryness to give a brown residue (23.25 g). The residue was purified by column chromatography on silica gel (Wako Gel C-200, 200 g) with an eluent system of chloroform:methanol:water=9:1:0.1→8:2:0.2. The active fraction (1.3883 g) was further purified by column chromatography on TOYOPEARL HW-40 with an eluent system of chloroform:methanol=1:1 to give an active fraction (1.1625 g), which was further subjected to column chromatography on silica gel under the same condition as described above to give an active fraction (303.9 mg) which showed a single spot on a normal phase thin layer chromatography. The product was dissolved in 2 ml of pyridine and subjected repeatedly to a reversed phase liquid chromatography [HPLC, CAPSULE PACK C18, SG-120, 10φ×250 mm (Shiseido K. K.), 97% methanol, 5 ml/min] to give colorless powders as the compounds of the present invention (1) (14.3 mg), (2) (19.0 mg), (3) (25.0 mg), (4) (73.1 mg), (5) (26.5 mg), (6) (25.7 mg), (7) (19.0 mg), (8) (11.6 mg), (9) (6.8 mg) at the retention times of 31.31 min, 38.25 min, 43.26 min, 48.70 min, 52.97 min, 57.45 min, 62.78 min, 67.47 min, and 73.02 min, respectively.

Compounds (1)–(9) showed the following spectral data.
Compound (1)
Optical rotation: $|\alpha|_D^{24}=+110.1°$ (pyridine, c=1.0).
High resolution FABMS analysis: 1181.7935 [(M–H)$^-$, theoretical value 1181.7893, based on $C_{60}H_{113}N_2O_{20}$ with an error of 4.2 mMU].
Infrared absorption spectrum: (KBr, cm$^{-1}$) 3370, 2920, 2850, 1645, 1535, 1470, 1040.
Melting point: 175.5°–177.0° C.
$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (1H, d, J=4.3 Hz), 5.60 (1H, d, J=3.7 Hz), 5.51 (1H, d, J=3.7 Hz), 5.30 (1H, dd, J=3.7, 11.0 Hz), 5.07 (1H, m), 5.02 (1H, m), 4.96 (1H, dd, J=3.7, 10.4 Hz), 4.85 (1H, dd, J=3.1, 11.0 Hz), 4.77 (1H, dd, J=3.1, 10.4 Hz), 4.74 (1H, m), 4.66 (1H, m), 4.64 (1H, dd, J=3.7, 7.9 Hz), 4.55 (1H, t, J=9.2 Hz), 4.45–4.51 (3H, m), 4.43 (1H, m), 4.39 (1H, bt, J=6.1 Hz), 4.35 (1H, dd, J=5.5, 10.4 Hz), 4.26 (1H, dd, J=7.9, 12.8 Hz), 4.10–4.22 (5H, m), 4.04 (1H, dd, J=3.7, 9.8 Hz), 3.95 (1H, t, J=9.2 Hz), 2.14 (2H, m), 2.04 (3H, s), 1.83–2.00 (3H, m), 1.59–1.76 (3H, m), 1.14–1.42 (56H, m), 0.85 (6H, m).

$^{13}$C-NMR spectrum (125 MHz, deuteropyridine+1% of heavy water): δ (ppm) 175.5 (s), 171.7 (s), 96.8 (d), 96.1 (d), 94.1 (d), 75.5 (d), 75.2 (d), 74.1 (d), 73.6 (d), 72.7 (d), 72.6 (d), 72.5 (d), 72.3 (d), 72.1 (d), 71.9 (d), 70.2 (d), 70.1 (d), 70.1 (d), 67.7 (t), 65.6 (d), 63.1 (t), 63.0 (t), 62.3 (t), 51.3 (d), 51.2 (d), 35.4 (t), 33.5 (t), 32.2 (t), 32.1 (t), 30.4 (t), 30.2 (t), 30.1 (t), 30.0 (t), 29.9 (t), 29.7 (t), 29.6 (t), 26.6 (t), 26.0 (t), 23.1 (q), 23.0 (t), 14.3 (q).

Compound (2)

Optical rotation: $|\alpha|_D^{24}$=+93.4° (pyridine, c=0.76).

High resolution FABMS analysis: 1195.8073 |(M–H)$^-$, theoretical value 1195.8050, based on $C_{61}H_{115}N_2O_{20}$ with an error of 2.3 mMU|.

Infrared absorption spectrum: (KBr, cm$^{-1}$) 3370, 2920, 2850, 1645, 1535, 1470, 1040.

Melting point: 177.0°–179.0° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (2H, m), 5.51 (1H, d, J=3.7 Hz), 5.30 (1H, m), 5.08 (1H, m), 5.02 (1H, m), 4.96 (1H, dd, J=3.7, 10.4 Hz), 4.85 (1H, dd, J=3.1, 11.0 Hz), 4.77 (1H, dd, J=3.1, 10.4 Hz), 4.74 (1H, m), 4.66 (1H, m), 4.64 (1H, m), 4.54 (1H, t, J=9.2 Hz), 4.42–4.51 (4H, m), 4.40 (1H, bt, J=6.1 Hz), 4.34 (1H, dd, J=5.5, 10.4 Hz), 4.25 (1H, dd, J=7.9, 12.8 Hz), 4.10–4.22 (5H, m), 4.04 (1H, dd, J=3.7, 9.8 Hz), 3.95 (1H, t, J=9.2 Hz), 2.14 (2H, m), 2.04 (3H, s), 1.84–2.00 (3H, m), 1.59–1.76 (3H, m), 1.14–1.44 (58H, m), 0.85 (6H, m).

$^{13}$C-NMR spectrum (125 MHz, deuteropyridine+1% of heavy water): δ (ppm) 175.5 (s), 171.7 (s), 96.8 (d), 96.1 (d), 94.1 (d), 75.5 (d), 75.2 (d), 74.1 (d), 73.6 (d), 72.7 (d), 72.6 (d), 72.5 (d), 72.3 (d), 72.1 (d), 71.9 (d), 70.2 (d), 70.1 (d), 70.1 (d), 67.7 (t), 65.6 (d), 63.1 (t), 63.0 (t), 62.3 (t), 51.3 (d), 51.2 (d), 35.4 (t), 33.5 (t), 32.2 (t), 32.1 (t), 30.4 (t), 30.2 (t), 30.1 (t), 30.0 (t), 29.9 (t), 29.7 (t), 29.6 (t), 26.6 (t), 26.0 (t), 23.1 (q), 23.0 (t), 14.3 (q).

Compound (3)

Optical rotation: $|\alpha|_D^{24}$=+107.2° (pyridine, c=1.0).

High resolution FABMS analysis: 1209.8273 |(M–H)$^-$, theoretical value 1209.8207, based on $C_{62}H_{117}N_2O_{20}$ with an error of 6.7 mMU|.

Infrared absorption spectrum: (KBr, cm$^{-1}$) 3370, 2920, 2850, 1645, 1535, 1470, 1040.

Melting point: 179.5°–183.0° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (2H, m), 5.51 (1H, d, J=3.7 Hz), 5.30 (1H, dd, J=3.7, 11.0 Hz), 5.06 (1H, m), 5.03 (1H, m), 4.98 (1H, dd, J=3.7, 10.4 Hz), 4.87 (1H, dd, J=3.1, 11.0 Hz), 4.81 (1H, dd, J=3.1, 10.4 Hz), 4.75 (1H, m), 4.68 (1H, m), 4.66 (1H, dd, J=3.7, 7.9 Hz), 4.40–4.60 (6H, m), 4.35 (1H, dd, J=5.5, 10.4 Hz), 4.10–4.32 (6H, m), 4.04 (1H, dd, J=3.7, 9.8 Hz), 3.95 (1H, t, J=9.2 Hz), 2.14 (2H, m), 2.09 (3H, s), 1.85–2.02 (3H, m), 1.61–1.78 (3H, m), 1.14–1.42 (57H, m), 0.85–0.91 (9H, m).

$^{13}$C-NMR spectrum (125 MHz, deuteropyridine+1% of heavy water): δ (ppm) 175.9 (s), 172.4 (s), 96.8 (d), 96.1 (d), 94.1 (d), 75.3 (d), 75.2 (d), 74.2 (d), 73.7 (d), 72.9 (d), 72.7 (d), 72.7 (d), 72.4 (d), 72.2 (d), 71.8 (d), 70.3 (d), 70.1 (d), 70.0 (d), 67.9 (t), 65.6 (d), 63.3 (t), 63.2 (t), 62.5 (t), 51.4 (d), 51.2 (d), 39.5 (t), 35.5 (t), 33.2 (t), 32.3 (t), 30.6 (t), 30.5 (t), 30.3 (t), 30.2 (t), 30.1 (t), 29.8 (t), 28.4 (d), 27.9 (t), 26.8 (t), 26.1 (t), 23.2 (q), 23.1 (t), 23.0 (q), 14.5 (q).

Compound (4)

Optical rotation: $|\alpha|_D^{24}$=+107.4° (pyridine, c=1.0).

High resolution FABMS analysis: 1209.8192 |(M–H)$^-$, theoretical value 1209.8207, based on $C_{62}H_{117}N_2O_{20}$ with an error of –1.5 mMU|.

Infrared absorption spectrum: (KBr, cm$^{-1}$) 3370, 2920, 2850, 1645, 1535, 1470, 1040.

Melting point: 183.0°–184.5° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (2H, m), 5.51 (1H, d, J=3.7 Hz), 5.30 (1H, dd, J=3.7, 11.0 Hz), 5.07 (1H, m), 5.02 (1H, m), 4.96 (1H, dd, J=3.7, 10.4 Hz), 4.85 (1H, dd, J=3.1, 11.0 Hz), 4.78 (1H, dd, J=3.1, 10.4 Hz), 4.74 (1H, m), 4.62–4.69 (2H, m), 4.55 (1H, t, J=9.2 Hz), 4.45–4.51 (4H, m), 4.42 (1H, bt, J=6.1 Hz), 4.35 (1H, dd, J=5.5, 10.4 Hz), 4.27 (1H, m), 4.10–4.22 (5H, m), 4.04 (1H, dd, J=3.7, 9.8 Hz), 3.95 (1H, t, J=9.2 Hz), 2.14 (2H, m), 2.07 (3H, s), 1.83–2.00 (3H, m), 1.59–1.76 (3H, m), 1.14–1.42 (60H, m), 0.87 (6H, m).

$^{13}$C-NMR spectrum (125 MHz, deuteropyridine+1% of heavy water): δ (ppm) 175.7 (s), 172.0 (s), 96.8 (d), 96.1 (d), 94.1 (d), 75.3 (d), 75.3 (d), 74.1 (d), 73.7 (d), 72.8 (d), 72.6 (d), 72.6 (d), 72.3 (d), 72.2 (d), 71.8 (d), 70.3 (d), 70.1 (d), 70.0 (d), 67.8 (t), 65.6 (d), 63.2 (t), 63.1 (t), 62.4 (t), 51.4 (d), 51.2 (d), 35.4 (t), 33.4 (t), 32.3 (t), 32.2 (t), 30.5 (t), 30.3 (t), 30.2 (t), 30.1 (t), 30.0 (t), 29.7 (t), 29.7 (t), 26.7 (t), 26.0 (t), 23.2 (q), 23.1 (t), 14.4 (q).

Compound (5)

Optical rotation: $|\alpha|_D^{24}$=+112.2° (pyridine, c=1.0).

High resolution FABMS analysis: 1223.8352 |(M–H)$^-$, theoretical value 1223.8363, based on $C_{63}H_{119}N_2O_{20}$ with an error of 1.1 mMU|.

Infrared absorption spectrum: (KBr, cm$^{-1}$) 3370, 2920, 2850, 1645, 1535, 1470, 1040.

Melting point: 188.0°–189.5° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (2H, m), 5.52 (1H, d, J=3.7 Hz), 5.30 (1H, dd, J=3.7, 11.0 Hz), 5.07 (1H, m), 5.02 (1H, m), 4.98 (1H, dd, J=3.7, 10.4 Hz), 4.87 (1H, dd, J=3.1, 11.0 Hz), 4.81 (1H, dd, J=3.1, 10.4 Hz), 4.75 (1H, m), 4.68 (1H, m), 4.66 (1H, dd, J=3.7, 7.9 Hz), 4.42–4.58 (6H, m), 4.36 (1H, dd, J=5.5, 10.4 Hz), 4.29 (1H, dd, J=7.9, 12.8 Hz), 4.10–4.26 (5H, m), 4.07 (1H, dd, J=3.7, 9.8 Hz), 3.92 (1H, t, J=9.2 Hz), 2.16 (2H, m), 2.09 (3H, s), 1.83–2.02 (3H, m), 1.60–1.77 (3H, m), 1.10–1.46 (59H, m), 0.85–0.91 (9H, m).

$^{13}$C-NMR spectrum (125 MHz, deuteropyridine+1% of heavy water): δ (ppm) 176.0 (s), 172.5 (s), 96.8 (d), 96.1 (d), 94.1 (d), 75.3 (d), 75.3 (d), 74.2 (d), 73.6 (d), 72.9 (d), 72.7 (d), 72.7 (d), 72.4 (d), 72.3 (d), 71.8 (d), 70.3 (d), 70.1 (d), 70.1 (d), 67.9 (t), 65.6 (d), 63.3 (t), 63.2 (t), 62.5 (t), 51.4 (d), 51.2 (d), 39.5 (t), 35.5 (t), 33.2 (t), 32.3 (t), 30.6 (t), 30.5 (t), 30.3 (t), 30.2 (t), 30.1 (t), 29.9 (t), 29.8 (t), 28.4 (d), 27.9 (t), 26.8 (t), 26.1 (t), 23.2 (q), 23.1 (t), 23.0 (q), 14.5 (q).

Compound (6)

Optical rotation: $|\alpha|_D^{24}$=+117.00° (pyridine, c=1.0).

High resolution FABMS analysis: 1223.8298 |(M–H)$^-$, theoretical value 1223.8363, based on $C_{63}H_{119}N_2O_{20}$, with an error of –6.5 mMU|.

Infrared absorption spectrum: (KBr, cm$^{-1}$) 3370, 2920, 2850, 1645, 1535, 1470, 1040.

Melting point: 183.0°–185.0° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (2H, m), 5.52 (1H, d, J=3.7 Hz), 5.30 (1H, dd, J=3.7, 11.0 Hz), 5.08 (1H, m), 5.03 (1H, m), 4.98 (1H, dd, J=3.7, 10.4 Hz), 4.87 (1H, dd, J=3.1, 11.0 Hz), 4.80 (1H, dd, J=3.1, 10.4 Hz), 4.75 (1H, m), 4.68 (1H, m), 4.66 (1H, dd, J=3.7, 7.9 Hz), 4.40–4.58 (6H, m), 4.36 (1H, dd, J=5.5, 10.4 Hz), 4.28 (1H, dd, J=7.9, 12.8 Hz), 4.10–4.25 (5H, m), 4.06 (1H, dd, J=3.7, 9.8 Hz), 3.92 (1H, t, J=9.2 Hz), 2.15 (2H, m), 2.08 (3H, s), 1.85–2.01 (3H, m), 1.59–1.78 (3H, m), 1.16–1.48 (62H, m), 0.87 (6H, m).

$^{13}$C-NMR spectrum (125 MHz, deuteropyridine+1% of heavy water): δ (ppm) 175.7 (s), 172.0 (s), 96.8 (d), 96.1 (d), 94.1 (d), 75.4 (d), 75.3 (d), 74.1 (d), 73.6 (d), 72.8 (d), 72.7 (d), 72.6 (d), 72.3 (d), 72.2 (d), 71.8 (d), 70.3 (d), 70.1 (d), 70.0 (d), 67.8 (t), 65.6 (d), 63.2 (t), 63.1 (t), 62.4 (t), 51.3 (d), 51.2 (d), 35.4 (t), 33.4 (t), 32.2 (t), 32.2 (t), 30.5 (t), 30.3 (t), 30.2 (t), 30.1 (t), 30.1 (t), 30.1 (t), 30.0 (t), 29.7 (t), 29.7 (t), 26.7 (t), 26.0 (t), 23.1 (q), 23.0 (t), 14.4 (q).

Compound (7)

Optical rotation: $[\alpha]_D^{24}$=+118.9° (pyridine, c=1.0).

High resolution FABMS analysis: 1237.8533 [(M–H)$^-$, theoretical value 1237.8520, based on $C_{64}H_{121}N_2O_{20}$ with an error of 1.3 mMU].

Infrared absorption spectrum: (KBr, cm$^{-1}$) 3370, 2920, 2850, 1645, 1535, 1470, 1040.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (1H, d, J=4.3 Hz), 5.60 (1H, d, J=3.7 Hz), 5.51 (1H, d, J=3.7 Hz), 5.30 (1H, dd, J=3.7, 11.0 Hz), 5.07 (1H, m), 5.02 (1H, m), 4.96 (1H, m), 4.86 (1H, m), 4.78 (1H, m), 4.74 (1H, m), 4.67 (1H, m), 4.64 (1H, m), 4.55 (1H, t, J=9.2 Hz), 4.42–4.51 (4H, m), 4.39 (1H, m), 4.35 (1H, dd, J=5.5, 10.4 Hz), 4.26 (1H, m), 4.10–4.22 (5H, m), 4.04 (1H, dd, J=3.7, 9.8 Hz), 3.94 (1H, t, J=9.2 Hz), 2.16 (2H, m), 2.06 (3H, s), 1.85–2.01 (3H, m), 1.59–1.79 (3H, m), 1.12–1.45 (61H, m), 0.83–0.89 (9H, m).

$^{13}$C-NMR spectrum (125 MHz, deuteropyridine+1% of heavy water): δ (ppm) 176.0 (s), 172.5 (s), 96.8 (d), 96.1 (d), 94.1 (d), 75.3 (d), 75.3 (d), 74.2 (d), 73.6 (d), 72.9 (d), 72.7 (d), 72.7 (d), 72.4 (d), 72.3 (d), 71.8 (d), 70.3 (d), 70.1 (d), 70.1 (d), 67.9 (t), 65.6 (d), 63.3 (t), 63.2 (t), 62.5 (t), 51.4 (d), 51.2 (d), 39.5 (t), 35.5 (t), 33.2 (t), 32.3 (t), 30.6 (t), 30.5 (t), 30.3 (t), 30.2 (t), 30.1 (t), 29.9 (t), 29.8 (t), 28.4 (t), 27.9 (t), 26.8 (t), 26.1 (t), 23.2 (q), 23.1 (t), 23.0 (q), 14.5 (q).

Compound (8)

Optical rotation: $[\alpha]_D^{24}$=+119.0° (pyridine, c=1.0).

High resolution FABMS analysis: 1237.8492 [(M–H)$^-$, theoretical value 1237.8520, based on $C_{64}H_{121}N_2O_{20}$ with an error of –2.8 mMU].

Infrared absorption spectrum: (KBr, cm$^{-1}$) 3370, 2920, 2850, 1645, 1535, 1470, 1040.

Melting point: 184.5°–186.5° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.62 (2H, m), 5.55 (1H, d, J=3.7 Hz), 5.31 (1H, dd, J=3.7, 11.0 Hz), 5.06 (2H, m), 5.00 (1H, dd, J=3.7, 10.4 Hz), 4.88 (1H, dd, J=3.1, 11.0 Hz), 4.83 (1H, dd, J=3.1, 10.4 Hz), 4.76 (1H, m), 4.70 (1H, m), 4.69 (1H, m), 4.47–4.59 (6H, m), 4.38 (1H, dd, J=5.5, 10.4 Hz), 4.10–4.34 (6H, m), 4.08 (1H, dd, J=3.7, 9.8 Hz), 3.92 (1H, t, J=9.2 Hz), 2.16 (2H, m), 2.12 (3H, s), 1.85–2.05 (3H, m), 1.64–1.78 (3H, m), 1.20–1.48 (64H, m), 0.89 (6H, m).

$^{13}$C-NMR spectrum (125 MHz, deuteropyridine+1% of heavy water): δ (ppm) 175.7 (s), 172.0 (s), 96.8 (d), 96.1 (d), 94.1 (d), 75.3 (d), 75.3 (d), 74.1 (d), 73.7 (d), 72.8 (d), 72.6 (d), 72.6 (d), 72.6 (d), 72.3 (d), 72.2 (d), 71.8 (d), 70.3 (d), 70.1 (d), 70.0 (d), 67.8 (t), 65.6 (d), 63.2 (t), 63.1 (t), 62.4 (t), 51.4 (d), 51.2 (d), 35.4 (t), 33.4 (t), 32.3 (t), 32.2 (t), 30.5 (t), 30.3 (t), 30.2 (t), 30.1 (t), 30.0 (t), 29.7 (t), 29.7 (t), 26.7 (t), 26.0 (t), 23.2 (q), 23.1 (t), 14.5 (q).

Compound (9)

Optical rotation: $[\alpha]_D^{24}$=+103.2° (pyridine, c=0.68).

High resolution FABMS analysis: 1251.8708 [(M–H)$^-$, theoretical value 1251.8676, based on $C_{65}H_{123}N_2O_{20}$ with an error of 3.2 mMU].

Infrared absorption spectrum: (KBr, cm$^{-1}$) 3370, 2920, 2850, 1645, 1535, 1470, 1040.

Melting point: 190.5°–191.5° C.

$^1$H-NMR spectrum (500 MHz, deuteropyridine+1% of heavy water): δ (ppm) 8.61 (1H, d, J=9.2 Hz), 8.49 (1H, d, J=9.2 Hz), 5.61 (1H, d, J=4.3 Hz), 5.60 (1H, d, J=3.7 Hz), 5.51 (1H, d, J=3.7 Hz), 5.30 (1H, dd, J=3.7, 11.0 Hz), 4.99–5.06 (2H, m), 4.96 (1H, dd, J=3.7, 10.4 Hz), 4.85 (1H, dd, J=3.1, 11.0 Hz), 4.77 (1H, dd, J=3.1, 10.4 Hz), 4.74 (1H, m), 4.66 (1H, m), 4.64 (1H, dd, J=3.7, 7.9 Hz), 4.55 (1H, t, J=9.2 Hz), 4.45–4.51 (3H, m), 4.45 (1H, m), 4.43 (1H, m), 4.35 (1H, m), 4.26 (1H, m), 4.10–4.22 (5H, m), 4.06 (1H, dd, J=3.7, 9.8 Hz), 3.99 (1H, t, J=9.2 Hz), 2.14 (2H, m), 2.02 (3H, s), 1.83–2.00 (3H, m), 1.59–1.76 (3H, m), 1.81–1.45 (63H, m), 0.81–0.89 (9H, m).

$^{13}$C-NMR spectrum (125 MHz, deuteropyridine+1% of heavy water): δ (ppm) 175.4 (s), 171.4 (s), 96.8 (d), 96.2 (d), 94.1 (d), 75.5 (d), 75.2 (d), 74.1 (d), 73.6 (d), 72.7 (d), 72.5 (d), 72.5 (d), 72.2 (d), 72.0 (d), 72.0 (d), 70.1 (d), 70.1 (d), 70.1 (d), 67.8 (t), 65.6 (d), 62.9 (t), 62.9 (t), 62.3 (t), 51.2 (d), 51.2 (d), 36.9 (t), 35.3 (t), 34.6 (d), 33.2 (t), 32.1 (t), 30.4 (t), 30.2 (t), 30.0 (t), 30.0 (t), 29.9 (t), 29.7 (t), 29.6 (t), 27.4 (t), 26.6 (t), 25.9 (t), 23.0 (q), 22.9 (t), 19.4 (q), 14.3 (q), 11.6 (q).

EXPERIMENTAL EXAMPLE 2: PREPARATION

A sponge Agelas axisera collected in the sea around Miyako-jima island, Okanawa was homogenized and lyophilized (951 g). The product was extracted with 2 liters of chloroform-methanol (1:1) for 24 hours, and the extract was evaporated to dryness under reduced pressure to give a brown extract (232 g). The extract was partitioned into 2 liters of water and 2 liters of ethyl acetate, and the ethyl acetate layer was evaporated to dryness to give a brown residue (65.0 g). In addition, an intermediate layer was obtained in an amount of 27.8 g. The residue was partitioned into 2 liters of 90% methanol and 2 liters of n-hexane, and the 90% methanol layer was evaporated to dryness to give a brown residue (53.7 g). The intermediate layer and the 90% methanol layer were purified by column chromatography on silica gel (Wako Gel C-200, 500 g) with an eluent system of chloroform:methanol:water=9:1:0.1→8:2:0.2. The active fraction (5.06 g) thus obtained was further purified by column chromatography on Sephadex LH-20 with an eluent system of chloroform:methanol=1:1 to give an active fraction (3.91 g), which was further subjected to column chromatography on silica gel (Wako Gel C-200, 100 g) with an eluent system of chloroform:methanol:water= 9:1:0.1→8:2:0.2 to give an active fraction (2.76 g). A 1.30 g portion of the product was dissolved in 2 ml of pyridine and subjected repeatedly to a reversed phase liquid chromatography [HPLC, D-ODS-5, S-5, 120A, 20ϕ×250 mm (K. K., YMC), 99% methanol, 10 ml/min] to give colorless powders as the compounds of the present invention (10) (30.3 mg), (11) (55.9 mg), (12) (245.7 mg), (13) (49.2 mg), (14) (115.4 mg), (15) (61.2 mg), (16) (55.0 mg), and (17) (30.1 mg) at the retention times of 30.5 min, 36.0 min, 43.1 min, 46.2 min, 50.7 min, 56.4 min, 58.9 min, and 63.5 min, respectively.

Compounds (10)–(17) showed the following spectral data.

Compound (10)

Optical rotation: $[\alpha]_D^{23}$=30 25.1° (pyridine, c=1.06).

High resolution FABMS analysis: 950.6779 [(M–H)$^-$, theoretical value 950.6786, based on $C_{50}H_{96}NO_{15}$ with an error of 0.7 mMU].

Infrared absorption spectrum: (KBr, cm$^{-1}$) 3400, 2950, 2870, 1645, 1535, 1475, 1080.

Melting point: 127.0°–130.0° C.

$^1$H-NMR spectrum (500 MHz, deuteropyridine+1% of heavy water, 35° C.): δ (ppm) 8.47 (1H, d, J=9.2 Hz), 5.87 (1H, bs), 5.44 (1H, d, J=3.7 Hz), 5.19 (1H, m), 4.93 (1H, m), 4.84 (1H, m), 4.78 (1H, bs), 4.68 (1H, d, J=3.1 Hz), 4.62 (1H, dd, J=3.7, 9.8 Hz), 4.57 (2H, m), 4.41 (2H, m), 4.25–4.32 (5H, m), 4.22 (1H, dd, J=5.5, 6.1 Hz), 4.17 (1H, dd, J=6.7, 9.1 Hz), 2.23 (1H, m), 2.14 (1H, m), 1.97 (1H, m), 1.88 (2H, m), 1.58–1.76 (3H, m), 1.14–1.45 (52H, m), 0.83 (6H, t, J=7.3 Hz).

$^{13}$C-NMR spectrum (125 MHz, deuteropyridine+1% of heavy water): δ (ppm) 175.3 (s), 110.7 (d), 100.9 (d), 85.6 (d), 82.4 (d), 78.7 (d), 78.6 (d), 76.0 (d), 72.3 (d), 72.3 (d), 72.2 (d), 72.1 (d), 70.2 (d), 68.4 (d), 68.1 (t), 64.1 (t), 62.4 (t), 50.6 (d), 35.3 (t), 35.3 (t), 33.9 (t), 32.0 (t), 30.3 (t), 30.1 (t), 29.9 (t), 29.8 (t), 29.8 (t), 29.5 (t), 26.3 (t), 25.7 (t), 22.8 (t), 14.2 (q).

Compound (11)

Optical rotation: $[\alpha]_D^{23}$=+27.3° (pyridine, c=2.96).

High resolution FABMS analysis: 964.6963 |(M–H)$^-$, theoretical value 964.6942, based on $C_{51}H_{98}NO_{15}$ with an error of 2.1 mMU|.

Infrared absorption spectrum: (KBr, cm$^{-1}$) 3400, 2950, 2870, 1645, 1535, 1475, 1080.

Melting point: 138.5°–142.0° C.

$^1$H-NMR spectrum (500 MHz, deuteropyridine+1% of heavy water): δ (ppm) 8.50 (1H, d, J=9.2 Hz), 5.87 (1H, s), 5.42 (1H, d, J=3.7 Hz), 5.18 (1H, m), 4.93 (1H, dd, J=3.7, 4.9 Hz), 4.84 (1H, dd, J=3.0, 5.5 Hz), 4.78 (1H, bs), 4.66 (1H, d, J=3.7 Hz), 4.61 (1H, dd, J=3.7, 9.8 Hz), 4.57 (1H, dd, J=3.7, 8.0 Hz), 4.53 (1H, dd, J=4.9, 10.4 Hz), 4.41 (2H, m), 4.25–4.32 (5H, m), 4.21 (1H, dd, J=4.2, 5.2 Hz), 4.17 (1H, dd, J=7.3, 14.0 Hz), 2.21 (1H, m), 2.13 (1H, m), 1.94 (1H, m), 1.85 (2H, m), 1.57–1.74 (3H, m), 1.10–1.45 (54H, m), 0.83 (6H, t, J=7.3 Hz).

$^{13}$C-NMR spectrum (125 MHz, deuteropyridine+1% of heavy water): δ (ppm) 175.4 (s), 110.7 (d), 100.9 (d), 85.7 (d), 82.3 (d), 78.7 (d), 78.6 (d), 75.9 (d), 72.3 (d), 72.3 (d), 72.3 (d), 72.1 (d), 70.1 (d), 68.4 (d), 68.1 (t), 64.0 (t), 62.4 (t), 50.7 (d), 35.3 (t), 33.9 (t), 32.0 (t), 30.3 (t), 30.1 (t), 29.9 (t), 29.9 (t), 29.8 (t), 29.8 (t), 29.5 (t), 29.5 (t), 26.3 (t), 25.7 (t), 22.8 (t), 14.2 (q).

Compound (12)

Optical rotation: $[\alpha]_D^{23}$=+27.7° (pyridine, c=2.07).

High resolution FABMS analysis: 978.7120 |(M–H)$^-$, theoretical value 978.7093, based on $C_{52}H_{100}NO_{15}$ with an error of 2.7 mMU|.

Infrared absorption spectrum: (KBr, cm$^{-1}$) 3400, 2950, 2870, 1645, 1535, 1475, 1080.

Melting point: 126.0°–131.0° C.

$^1$H-NMR spectrum (500 MHz, deuteropyridine+1% of heavy water, 37° C.): δ (ppm) 8.50 (1H, d, J=9.2 Hz), 5.91 (1H, s), 5.46 (1H, d, J=3.7 Hz), 5.20 (1H, m), 4.96 (1H, m), 4.87 (1H, m), 4.82 (1H, bs), 4.71 (1H, bs), 4.65 (1H, dd, J=3.7, 9.8 Hz), 4.60 (1H, m), 4.58 (1H, dd, J=4.9, 10.4 Hz), 4.44 (2H, m), 4.27–4.36 (5H, m), 4.24 (1H, m), 4.19 (1H, dd, J=4.3, 11.0 Hz), 2.25 (1H, m), 2.18 (1H, m), 2.00 (1H, m), 1.90 (2H, m), 1.64–1.80 (3H, m), 1.19–1.50 (56H, m), 0.88 (6H, t, J=6.7 Hz).

$^{13}$C-NMR spectrum (125 MHz, deuteropyridine+1% of heavy water, 37° C.): δ (ppm) 175.6 (s), 110.9 (d), 101.1 (d), 86.1 (d), 82.5 (d), 78.9 (d), 78.8 (d), 76.2 (d), 72.6 (d), 72.5 (d), 72.5 (d), 72.4 (d), 70.4 (d), 68.7 (d), 68.4 (t), 64.2 (t), 62.6 (t), 51.0 (d), 35.5 (t), 34.1 (t), 32.2 (t), 30.5 (t), 30.2 (t), 30.1 (t), 30.0 (t), 29.7 (t), 29.6 (t), 26.5 (t), 25.9 (t), 23.0 (t), 14.3 (q).

Compound (13)

Optical rotation: $[\alpha]_D^{23}$=+45.1° (pyridine, c=2.14).

High resolution FABMS analysis: 992.7269 |(M–H)$^-$, theoretical value 992.7249, based on $C_{53}H_{102}NO_{15}$ with an error of 2.0 mMU|.

Infrared absorption spectrum: (KBr, cm$^{-1}$) 3400, 2950, 2870, 1645, 1535, 1475, 1080.

Melting point: 147.0°–150.0° C.

$^1$H-NMR spectrum (500 MHz, deuteropyridine+1% of heavy water): δ (ppm) 8.52 (1H, d, J=9.2 Hz), 5.90 (1H, s), 5.42 (1H, d, J=4.2 Hz), 5.19 (1H, m), 4.95 (1H, dd, J=3.6, 4.9 Hz), 4.86 (1H, dd, J=3.1, 4.9 Hz), 4.81 (1H, bs), 4.68 (1H, d, J=3.1 Hz), 4.63 (1H, dd, J=3.7, 10.4 Hz), 4.59 (1H, dd, J=3.7, 7.9 Hz), 4.55 (1H, dd, J=4.9, 10.4 Hz), 4.43 (2H, m), 4.25–4.33 (5H, m), 4.23 (1H, dd, J=3.1, 6.1 Hz), 4.16 (1H, dd, J=3.1, 6.7 Hz), 2.22 (1H, m), 2.14 (1H, m), 1.96 (1H, m), 1.87 (2H, m), 1.57–1.74 (3H, m), 1.05–1.43 (55H, m), 0.82 (9H, m).

$^{13}$C-NMR spectrum (125 MHz, deuteropyridine+1% of heavy water): δ (ppm) 175.8 (s), 111.0 (d), 101.1 (d), 85.9 (d), 82.7 (d), 78.9 (d), 78.9 (d), 76.0 (d), 72.6 (d), 72.6 (d), 72.6 (d), 72.4 (d), 70.4 (d), 68.8 (d), 68.4 (t), 64.3 (t), 62.7 (t), 51.0 (d), 39.5 (t), 35.6 (t), 34.0 (t), 32.3 (t), 30.6 (t), 30.4 (t), 30.4 (t), 30.2 (t), 30.1 (t), 29.8 (t), 28.4 (d), 27.9 (t), 26.6 (t), 26.0 (t), 23.1 (t), 23.0 (q), 14.5 (q).

Compound (14)

Optical rotation: $[\alpha]_D^{23}$=+34.0° (pyridine, c=2.96).

High resolution FABMS analysis: 992.7285 |(M–H)$^-$, theoretical value 992.7249, based on $C_{53}H_{102}NO_{15}$ with an error of 3.6 mMU|.

Infrared absorption spectrum: (KBr, cm$^{-1}$) 3400, 2950, 2870, 1645, 1535, 1475, 1080.

Melting point: 138.0°–142.5° C.

$^1$H-NMR spectrum (500 MHz, deuteropyridine+1% of heavy water): δ (ppm) 8.51 (1H, d, J=9.1 Hz), 5.88 (1H, s), 5.44 (1H, d, J=3.7 Hz), 5.19 (1H, m), 4.94 (1H, dd, J=3.6, 5.4 Hz), 4.86 (1H, m), 4.79 (1H, bs), 4.67 (1H, d, J=3.1 Hz), 4.62 (1H, dd, J=3.7, 9.8 Hz), 4.57 (1H, dd, J=3.7, 8.0 Hz), 4.54 (1H, dd, J 4.9, 11.0 Hz), 4.40 (2H, m), 4.24–4.33 (5H, m), 4.22 (1H, m), 4.14 (1H, dd, J=7.3, 13.4 Hz), 2.22 (1H, m), 2.14 (1H, m), 1.95 (1H, m), 1.87 (2H, m), 1.57–1.74 (3H, m), 1.05–1.43 (58H, m), 0.82 (6H, t, J=6.7 Hz).

$^{13}$C-NMR spectrum (125 MHz, deuteropyridine+1% of heavy water): δ (ppm) 175.2 (s), 110.7 (d), 101.1 (d), 86.0 (d), 82.6 (d), 78.9 (d), 78.7 (d), 76.4 (d), 72.5 (d), 72.5 (d), 72.4 (d), 72.3 (d), 70.4 (d), 68.5 (d), 68.3 (t), 64.4 (t), 62.7 (t), 50.7 (d), 35.6 (t), 34.3 (t), 32.1 (t), 30.4 (t), 30.2 (t), 30.0 (t), 30.0 (t), 29.9 (t), 29.9 (t), 29.6 (t), 29.6 (t), 26.4 (t), 25.8 (t), 22.9 (t), 14.3 (q).

Compound (15)

Optical rotation: $[\alpha]_D^{23}$=+35.2° (pyridine, c=3.19).

High resolution FABMS analysis: 1006.7430 |(M–H)$^-$, theoretical value 1006.7406, based on $C_{54}H_{104}NO_{15}$ with an error of 2.4 mMU|.

Infrared absorption spectrum: (KBr, cm$^{-1}$) 3400, 2950, 2870, 1645, 1535, 1475, 1080.

Melting point: 125.0°–129.5° C.

$^1$H-NMR spectrum (500 MHz, deuteropyridine+1% of heavy water): δ (ppm) 8.51 (1H, d, J=9.2 Hz), 5.89 (1H, s), 5.41 (1H, d, J=4.3 Hz), 5.17 (1H, m), 4.94 (1H, dd, J=3.6, 5.4 Hz), 4.85 (1H, m), 4.80 (1H, bs), 4.67 (1H, d, J=3.1 Hz), 4.62 (1H, dd, J=4.2, 9.8 Hz), 4.59 (1H, dd, J=3.7, 7.9 Hz), 4.55 (1H, dd, J=4.9, 10.4 Hz), 4.38–4.44 (2H, m), 4.25–4.33 (5H, m), 4.21 (1H, dd, J=3.1, 6.1 Hz), 4.15 (1H, dd, J=3.1, 6.7 Hz), 2.20 (1H, m), 2.13 (1H, m), 1.94 (1H, m), 1.87 (2H, m), 1.57–1.74 (3H, m), 1.05–1.43 (57H, m), 0.81 (9H, m).

$^{13}$C-NMR spectrum (125 MHz, deuteropyridine+1% of heavy water): δ (ppm) 175.4 (s), 110.7 (d), 100.8 (d), 85.6

(d), 82.3 (d), 78.6 (d), 78.6 (d), 75.6 (d), 72.2 (d), 72.2 (d), 72.2 (d), 72.1 (d), 70.1 (d), 68.4 (d), 68.0 (t), 63.9 (t), 62.3 (t), 50.7 (d), 39.1 (t), 35.3 (t), 33.7 (t), 31.9 (t), 30.2 (t), 30.0 (t), 29.9 (t), 29.4 (t), 28.0 (d), 27.5 (t), 26.3 (t), 25.7 (t), 22.8 (t), 22.6 (q), 14.1 (q).

Compound (16)

Optical rotation: $[\alpha]_D^{23}=+34.6°$ (pyridine, c=2.41).

High resolution FABMS analysis: 1006.7430 $[(M-H)^-$, theoretical value 1006.7406, based on $C_{54}H_{104}NO_{15}$ with an error of 2.4 mMU].

Infrared absorption spectrum: (KBr, $cm^{-1}$) 3400, 2950, 2870, 1645, 1535, 1475, 1080.

Melting point: 125.0°–129.0° C.

$^1$H-NMR spectrum (500 MHz, deuteropyridine+1% of heavy water): δ (ppm) 8.51 (1H, d, J=9.1 Hz), 5.88 (1H, s), 5.41 (1H, d, J=3.7 Hz), 5.16 (1H, m), 4.93 (1H, dd, J=3.6, 5.4 Hz), 4.84 (1H, m), 4.79 (1H, bs), 4.67 (1H, d, J=3.1 Hz), 4.61 (1H, dd, J=3.7, 9.8 Hz), 4.58 (1H, dd, J =3.7, 8.0 Hz), 4.53 (1H, dd, J=4.9, 11.0 Hz), 4.40 (2H, m), 4.24–4.33 (5H, m), 4.21 (1H, m), 4.14 (1H, dd, J=7.3, 13.4 Hz), 2.20 (1H, m), 2.12 (1H, m), 1.95 (1H, m), 1.86 (2H, m), 1.57–1.74 (3H, m), 1.05–1.43 (60H, m), 0.82 (6H, m).

$^{13}$C-NMR spectrum (125 MHz, deuteropyridine+1% of heavy water): δ (ppm) 175.1 (s), 110.7 (d), 101.1 (d), 86.0 (d), 82.6 (d), 78.9 (d), 78.7 (d), 76.4 (d), 72.5 (d), 72.5 (d), 72.4 (d), 72.2 (d), 70.4 (d), 68.5 (d), 68.3 (t), 64.3 (t), 62.7 (d), 50.6 (d), 35.5 (t), 34.3 (t), 32.1 (t), 30.4 (t), 30.1 (t), 30.0 (t), 29.9 (t), 29.9 (d), 29.9 (t), 29.6 (t), 29.6 (t), 26.4 (t), 25.8 (t), 22.9 (t), 14.2 (q).

Compound (17)

Optical rotation: $[\alpha]_D^{23}=+39.5°$ (pyridine, c=1.14).

High resolution FABMS analysis: 1020.7537 $[(M-H)^-$, theoretical value 1020.7562, based on $C_{55}H_{106}NO_{15}$ with an error of 2.5 mMU].

Infrared absorption spectrum: (KBr, $cm^{-1}$) 3400, 2950, 2870, 1645, 1535, 1475, 1080.

Melting point: 124.5°–128.0° C.

$^1$H-NMR spectrum (500 MHz, deuteropyridine+1% of heavy water): δ (ppm) 8.51 (1H, d, J=9.2 Hz), 5.90 (1H, s), 5.45 (1H, d, J=3.7 Hz), 5.20 (1H, m), 4.96 (1H, dd, J=3.1, 5.5 Hz), 4.87 (1H, dd, J=3.0, 5.5 Hz), 4.80 (1H, bs), 4.69 (1H, d, J=3.0 Hz), 4.64 (1H, dd, J=3.6, 9.8 Hz), 4.59 (1H, dd, J=3.7, 8.0 Hz), 4.56 (1H, dd, J=4.9, 10.4 Hz), 4.39–4.46 (2H, m), 4.25–4.33 (5H, m), 4.23 (1H, dd, J=3.6, 6.1 Hz), 4.16 (1H, dd, J=7.9, 14.6 Hz), 2.22 (1H, m), 2.14 (1H, m), 1.96 (1H, m), 1.89 (2H, m), 1.57–1.74 (3H, m), 1.02–1.46 (59H, m), 0.82 (9H, m).

$^{13}$C-NMR spectrum (125 MHz, deuteropyridine+1% of heavy water): δ (ppm) 175.4 (s), 110.7 (d), 100.9 (d), 85.7 (d), 82.4 (d), 78.6 (d), 78.6 (d), 75.8 (d), 72.3 (d), 72.3 (d), 72.3 (d), 72.2 (d), 70.1 (d), 68.4 (t), 68.1 (t), 64.0 (t), 62.4 (t), 50.7 (d), 39.1 (t), 35.3 (t), 33.8 (t), 32.0 (t), 30.3 (t), 30.1 (t), 29.9 (t), 29.9 (t), 28.1 (d), 27.6 (t), 26.3 (t), 25.7 (t), 22.8 (t), 22.7 (t), 14.2 (q).

EXPERIMENTAL EXAMPLE 3: PREPARATION BY SYNTHESIS

The synthetic methods and physico-chemical properties of the compounds according to the present invention are shown below (see the reaction scheme in FIG. 2 on the synthetic methods).

Synthesis of Compound 18

D-lyxose (20 g, 0.133 mole) was suspended in 300 ml of acetone dehydrated with calcium chloride, 0.05 ml of concentrated sulfuric acid was added, and the mixture was stirred at room temperature for 18 hours before neutralization with 10.0 g of Molecular Sieves 4A. The mixture was filtered, and the residue was washed with acetone sufficiently. The washes were combined, concentrated under reduced pressure, and directly used in the following reaction without purification.

Synthesis of Compound 19

The total amount of Compound 18 obtained in the above reaction was dissolved in 168 ml of methylene chloride, and 10.0 ml of pyridine and 39.0 g of trityl chloride were added. The mixture was stirred at 32° C. for 4 hours. After 7.8 ml of ethanol was added and the mixture was further stirred, the mixture was washed with a saturated aqueous ammonium chloride solution. The mixture was further washed with a saturated aqueous sodium hydrogen carbonate solution and saturated brine in this sequence. To the syrup product obtained by concentrating the mixture was added 20 ml of ethyl acetate to form a solution, to which 40 ml of hexane was added gradually. When the solution turned slightly turbid, it was left standing in the presence of seed crystals at 0° C. Crystals thus obtained was separated by filtration and washed with a mixed solvent of hexan/ethyl acetate=8/1. Primary crystals were obtained in an amount of 44.4 g, and secondary crystals were obtained in an amount of 5.6 g from the mother liquor. The yield was 86.8%.

M.p. 174°–176° C.; FD-MS=432 ($C_{27}H_{28}O_5$; MW=432.19); IR ($cm^{-1}$, KBr): 3530, 3400, 3050, 2950, 2880, 1600, 1490, 1450, 1375, 1215, 1070; $^1$H-NMR (500 MHz/CDCl$_3$): δ (ppm) 7.48 (6H, d, J=7.3 Hz), 7.29 (6H, t, J=7.3 Hz), 7.22 (3H, t, J=7.3 Hz), 5.38 (1H, d, J=2.4 Hz), 4.75 (1H, dd, J=5.5 Hz, 3.7 Hz), 4.59 (1H, d, J=6.1 Hz), 4.32–4.34 (1H, m), 3.43 (1H, dd, J=4.9 Hz, 9.8 Hz), 3.39 (1H, dd, J=6.7 Hz, 9.8 Hz), 2.33 (1H, d, J=2.4 Hz), 1.29 (3H, s), 1.28 (3H, s).

Synthesis of Compound 20

Triphenylphosphine in an amount of 96.0 g was added to 96.4 g of 1-bromotridecane, and the mixture was stirred at 140° C. for 4.5 hours. The mixture was gradually allowed to cool and dissolved in 500 ml of tetrahydrofuran. The solution was cooled to 0° C. and stirred for 15 minutes while adding dropwise 146.4 ml of a 2.5N n-butyl lithium solution. To the mixture was added a solution of Compound 19 in tetrahydrofuran (79 g/150 ml). The mixture was stirred for 18 hours while the temperature was slowly raised up to room temperature. After the mixture was concentrated under reduced pressure, it was diluted with 1,000 ml of a mixed solvent of hexane/methanol/water=10/7/3 followed by 40 ml of a saturated aqueous ammonium chloride solution for separation. The methanol/water layer was extracted again with 500 ml of hexane. The combined hexane layer thus obtained was dried over anhydrous magnesium sulfate, concentrated under reduced pressure, and finally dried sufficiently under reduced pressure with a vacuum pump to give a crude product of Compound 20 in the form of syrup. The product was directly used in the next reaction without further purification.

Synthesis of Compound 21

The total amount of Compound 20 obtained in the preceding reaction was diluted with 600 ml of methylene chloride and 200 ml of pyridine, and reacted with 16.95 ml of methanesulfonyl chloride with stirring at 31° C. for 24 hours. Ethanol (13 ml) was added, and the mixture was concentrated under reduced pressure with stirring at room temperature for 1 hour. A mixed solvent of hexane/methanol/water=10/7/3 in an amount of 1,000 ml was added for separation. The methanol/water layer was re-extracted thrice with 200 ml of hexane. The combined hexane layer thus obtained was dried over anhydrous magnesium sulfate, concentrated under reduced pressure, and finally dried sufficiently under reduced pressure with a vacuum pump to give a crude product of Compound 21 in the form of syrup. The product was directly used in the next reaction without further purification.

Synthesis of Compound 22

The total amount of Compound 21 obtained in the preceding step was dissolved in 900 ml of methylene chloride and 600 ml of methanol. Concentrated hydrochloric acid (124 ml) was added, and the mixture was stirred at room temperature for 5 hours. After neutralization with sodium hydrogen carbonate, the mixture was separated by filtration. The residue was washed with ethyl acetate, combined with the filtrate for concentration under reduced pressure. The residue was triturated with ethyl acetate, and washed with saturated brine. The aqueous layer was re-extracted thrice with ethyl acetate, and the combined ethyl acetate layer thus obtained was dried over anhydrous magnesium sulfate, concentrated under reduced pressure, and crystallized from hexane. The primary crystals were obtained in an amount of 41.0 g, and the secondary crystals were obtained in an amount of 9.40 g. The overall yield throughout the three steps was 70.0%.

M.p.: 66°–67° C.; FD-MS=377 (M -$H_2O)^+$, ($C_{19}H_{38}O_6S$; MW=394.57); IR (cm$^{-1}$, KBr): 3500, 3350, 2920, 2850, 1465, 1440, 1355, 1330, 1160, 1030, 930; $^1$H-NMR (500 MHz/CDCl$_3$+1 drop of $D_2O$); E/Z mixture (3:7): δ (ppm) 5.86 (0.3H, dt, J=7.3 Hz, 14.7 Hz), 5.77 (0.7H, dt, J=7.3 Hz, 10.4 Hz), 5.55 (0.3H, br. dd, J=7.3 Hz, 14.7 Hz), 5.49 (0.7H, br. t, J=9.8 Hz), 4.91–4.97 (1H, m), 4.51 (0.7H, br. t, J=9.8 Hz), 4.11 (0.3H, br. t, J=7.3 Hz), 3.94–4.03 (2H, m), 3.67–3.73 |1H (3.70, dd, J=3.1 Hz, 6.7 Hz), (3.69, dd, J=3.1 Hz, 7.3 Hz)|, 3.20 (2.1H, s), 3.19 (0.9H, s), 2.05–2.22 (2H, m), 1.22–1.43 (20H, m), 0.88 (3H, t, J=6.7 Hz).

Synthesis of Compound 23

To the solution of Compound 22 (24.4 g) in 244 ml of tetrahydrofuran was added 2.44 g of 5% palladium-barium sulfate. The reactor was purged with hydrogen gas, and the mixture was stirred at room temperature under hydrogen atmosphere for 20 hours. After the mixture was diluted with 200 ml of a mixed solvent of chloroform/methanol=1:1, it was filtered through Celite, and the residue was washed with a mixture of chloroform/methanol=1:1. The filtrate and the wash were combined, concentrated under reduced pressure and crystallized from ethyl acetate. Crystalline products obtained were washed well with hexane. The primary crystals were obtained in an amount of 21.5 g, and the secondary crystals were obtained in an amount of 0.64 g.

The yield was 91.3%.

M.p.: 124°–126° C.; FD-MS=397 ($C_{19}H_{40}O_6S$; MW=396.59); $|α|_D^{23}$=+7.52° (c=1.50, $C_5H_5N$); IR (cm$^{-1}$, KBr): 3500, 3380, 3220,2920, 2850,1470, 1430, 1360,1330, 1165, 1095, 930; $^1$H-NMR (500 MHz/CDCl$_3$-CD$_3$OD=1:1): δ (ppm) 4.93–4.96 (1H, m), 3.91 (1H, dd, J=6.7 Hz, 12.2 Hz), 3.85 (1H, dd, J=4.9 Hz, 12.2 Hz), 3.54–3.60 (1H, m), 3.50 (1H, dd, J =1.8 Hz, 8.5 Hz), 3.19 (3H, s), 1.75–1.83 (1H, m), 1.53–1.62 (1H, m), 1.21–1.45 (24H, m), 0.89 (3H, t, J=6.7 Hz).

Synthesis of Compound 24

To a solution of Compound 23 (8.94 g, 22.5 mmole) in 72 ml of anhydrous DMF was added 2.93 g of NaN$_3$. The mixture was heated to 95° C. in an oil bath, and stirred under heating at this temperature for 4 hours. After the disappearance of the starting material was confirmed by TLC (hexane:acetone=3:2), the reaction mixture was concentrated under reduced pressure. Ethyl acetate was added to the residual concentrate, and the mixture was washed with water. The aqueous layer was re-extracted with an equivalent volume of ethyl acetate. The combined ethyl acetate layer was washed with saturated brine, dried over anhydrous magnesium sulfate, concentrated under reduced pressure, and finally dried sufficiently under reduced pressure with a vacuum pump. The product was directly used in the next reaction without further purification.

Synthesis of Compound 25

To the total amount of powdery product obtained in the above step was added 45 ml of dichloromethane followed by 7.53 g of TrCl. Then, 14 ml of pyridine was added, and the mixture was stirred at room temperature for 16 hours. After the disappearance of the starting material was confirmed by TLC (hexane:ethyl acetate 2:1), the reaction was terminated with 1.8 ml of ethanol, and the mixture was further stirred for 30 minutes. The reaction mixture was washed with a saturated aqueous sodium hydrogen carbonate solution, a saturated aqueous ammonium chloride solution and brine in this sequence, dried over anhydrous magnesium sulfate, and concentrated under reduced pressure. The syrup thus obtained was purified by column chromatography on silica gel (hexane:ethyl acetate=10:1) to give Compound 25 in an amount of 6.93 g (yield 52%).

FD-MS=585 ($C_{37}H_{51}N_3O_3$; MW=585.82); $|α|_D^{23}$=+ 11.86° (c=0.86, CHCl$_3$); IR (cm$^{-1}$, film): 3425, 2924, 2854, 2098, 1491, 1466, 1448, 1267, 1223, 1074, 1034; $^1$H-NMR (500 MHz/CDCl$_3$+1 drop of $D_2O$): δ (ppm) 7.24–7.61 (15H, m), 3.62–3.66 (2H, m), 3.51–3.57 (2H, m), 3.42 (1H, dd, J=6.0 Hz, 10.4 Hz), 1.23–1.56 (26H, m), 0.88 (3H, t, J=6.7 Hz).

Synthesis of Compound 26

To a solution of 21.73 g of Compound 25 in the form of syrup was added portionwise 3.57 g of 60% sodium hydride. After the mixture stirred at room temperature for 40 minutes, 9.71 ml (1.05 eq.) of benzyl bromide was added dropwise, and the mixture was stirred for 2.5 hours while the temperature was slowly raised up to room temperature. After the disappearance of the raw material was confirmed by TLC (hexane:ethyl acetate=10:1), crashed ice was added to the mixture to terminate the reaction. The reaction mixture was diluted with 50 ml of water and extracted thrice with ethyl acetate. The ethyl acetate layer was washed thrice with brine dried over anhydrous magnesium sulfate, and concentrated under reduced pressure. The syrup thus obtained was purified by column chromatography on silica gel (hexane:ethyl acetate=100:1) to give Compound 26 in an amount of 23.97 g (yield 84.4%).

FD-MS=738 (M-$N_2)^+$, ($C_{51}H_{63}N_3O_3$; MW=766.07); $|α|_D^{23}$=+9.75° (c=0.97, CHCl$_3$); IR (cm$^{-1}$, film): 3062, 3031, 2925, 2854, 2096, 1492, 1465, 1450; $^1$H-NMR (500 MHz/CDCl$_3$): δ (ppm) 7.07–7.48 (25H, m), 4.57 (1H, d, J=11.0 Hz), 4.44 (1H, d, J=11.0 Hz), 4.41 (2H, s), 3.73–3.79 (1H, m), 3.46–3.56 (2H, m), 3.37 (1H, dd, J=8.6 Hz, 10.4 Hz), 1.20–1.64 (26H, m), 0.88 (3H, t, J =6.7 Hz).

Synthesis of Compound 27

To a solution of Compound 26 as the raw material (25.35 g, 33.14 mmol) in 1-propanol (200 ml) and methanol (25 ml) were added ammonium formate (16.72 g) and 10% palladium-carbon (1.0 g), and the mixture was stirred at room temperature for 16 hours. After the disappearance of the raw material and the appearance of the aimed product were confirmed by TLC (hexane:acetone=3:1), the reaction mixture was diluted with 50 ml of ethyl acetate, filtered through celite, washed with ethyl acetate, and concentrated under reduced pressure. The residual concentrate was diluted with ethyl acetate and washed twice with a saturated aqueous sodium hydrogen carbonate. The aqueous layer was re-extracted with ethyl acetate, and the combined ethyl acetate layer was washed with brine, dried over anhydrous magnesium sulfate, concentrated under reduced pressure, and azeotropically distilled with toluene. The product was used in the next reaction without further purification.

Synthesis of Compound 28

To a solution of the total amount of Compound 27 obtained in the previous reaction in the form of syrup in 250 ml of methylene chloride were added 12.49 g of cerotic acid and 7.13 g of WSC hydrochloride. The mixture was heated under reflux in an oil bath at about 50° C. for 2 hours. The raw material still observed in TLC (hexane:acetone=3:1), 620 mg of cerotic acid and 360 mg of WSC hydrochloride were added, and the mixture was further heated under reflux for 1 hour. The reaction mixture was cooled to room temperature, washed with a 0.5N aqueous hydrochloric acid solution, brine, a saturated aqueous sodium hydrogen carbonate and brine in this sequence, dried over anhydrous magnesium sulfate, concentrated under reduced pressure, and finally dried sufficiently under reduced pressure with a vacuum pump. The product was directly used in the next reaction without further purification.

Synthesis of Compound 29

To a solution of the total amount of Compound 28 obtained in the previous reaction in the form of syrup in the mixture of 120 ml of methylene chloride and 30 ml of methanol was added dropwise 3.0 ml of a 10% hydrochloric acid-methanol solution, and the mixture was stirred at room temperature for about 2 hours. After confirming the completion of the reaction by TLC (hexane:acetone=3:1), the mixture was neutralized with sodium hydrogen carbonate. After filtration through Celite, the mixture was washed twice with brine, dried over anhydrous magnesium sulfate, and concentrated under reduced pressure. The concentrate was distilled azeotropically with toluene, dissolved in acetone under heating, and stored at 0° C. to give white pricipitates in an amount of 22.2 g. The overall yield throughout the three steps were 76.6%.

M.p.: 75°–76.5° C.; FD-MS=876, ($C_{58}H_{101}NO_4$; MW=876.43); $[\alpha]_D^{23}$=−29.7° (c=0.675, $CHCl_3$); IR ($cm^{-1}$, KBr): 3334, 2918, 2850, 1637, 1618, 1548, 1469, 1103, 1052; $^1$H-NMR (500 MHz/$CDCl_3$): δ (ppm) 7.30–7.47 (10H, m), 6.07 (1H, d, J=7.9 Hz), 4.72 (1H, d, J=11.6 Hz), 4.66 (1H, d, J=11.6 Hz), 4.61 (2H, d, J=11.6 Hz), 4.24–4.32 (1H, m), 4.45 (1H, d, J=11.6 Hz), 4.00 (1H, dt, Jt=7.3 Hz, Jd=4.3 Hz), 3.67–3.72 (2H, m), 3.61 (1H, ddd, J=4.3 Hz, 11.6 Hz, 8.6 Hz), 3.05 (1H, dd, J=4.3 Hz, 8.5 Hz), 1.94–2.05 (2H, m), 1.15–1.69 (72H, m), 0.88 (6H, t, J=6.1 Hz).

Synthesis of Compound 30

Compound 29 (289.0 mg, 0.33 mmol), stannous chloride (147.0 mg, 0.78 mmol), silver perchlorate (160.8 mg, 0.78 mmol) and Molecular Sieves-4A (600 mg) were suspended in 7.5 ml of tetrahydrofuran, and the suspension was stirred at room temperature for 30 minutes. After the suspension was cooled to −10° C., a solution of α-6-O-(tetra-O-benzylgalactopyranosyl)-2,3,4-tri-O-benzylglucopyranosyl fluoride (643.6 mg, 0.66 mM) in tetrahydrofuran (3 ml) was added to the suspension. After the temperature was slowly raised up to room temperature, the reaction mixture was stirred for 2 hours, filtered through celite, concentrated to dryness, and purified by column chromatography on silica gel (acetone:n-hexane=3:17) to give Compound 30 (129) in an amount of 33.7 mg (5.6%).

$^1$H-NMR (500 MHz/$CDCl_3$): δ (ppm) 7.14–7.38 (45H, m), 5.87 (1H, d, J=8.6 Hz), 5.01 (1H, d, J=3.7 Hz), 4.35–4.94 (19H, m), 4.22 (1H, m), 4.03 (1H, dd, J=3.7 Hz, 9.8 Hz), 3.86–3.94 (5H, m), 3.84 (1H, dd, J=3.1 Hz, 6.7 Hz), 3.73–3.82 (3H, m), 3.67 (2H, m), 3.46–3.55 (3H, m), 3.33 (1H, dd, J=3.7, 9.8 Hz), 1.95 (1H, m), 1.91 (1H, m), 1.64 (2H, m), 1.48 (2H, m), 1.10–1.34 (68H, m), 0.88 (6H, t, J=6.7 Hz).

Synthesis of Compound 31

To a solution of Compound 30 (31.4 mg) in ethyl acetate (1.5 ml) was added palladium black (40 mg), and the mixture was stirred under hydrogen atmosphere at room temperature for 16 hours. The reaction mixture was filtered through Celite and purified by column chromatography on silica gel (chloroform:methanol:water=9:1:0.1) to give Compound 31 in an amount of 13.0 mg (74.3%).

Optical rotation: $[\alpha]_D^{23}$=+82.7° (pyridine, c=0.03).

High resolution FABMS analysis: 1018.7719 |(M-H)⁻, theoretical value 1018.7776, based on $C_{56}H_{108}NO_{14}$ with an error of 5.7 mMU|.

Infrared absorption spectrum: (KBr, $cm^{-1}$) 3400, 2950, 2870, 1645, 1535, 1475, 1080.

Melting point: 133.0°–136.5° C.

$^1$H-NMR spectrum (500 MHz, deuteropyridine+1% of heavy water): δ (ppm) 8.39 (1H, d, J=8.6 Hz), 5.39 (2H, d, J=3.7 Hz), 5.11 (1H, m), 4.62 (1H, dd, J=5.3, 10.4 Hz), 4.57 (1H, dd, J=3.7, 9.3 Hz), 4.53 (1H, t, J=6.0 Hz), 4.48 (2H, m), 4.45 (1H, dd, J=3.1, 6.7 Hz), 4.37–4.44 (3H, m), 4.32 (2H, m), 4.23 (2H, m), 4.18 (1H, d, J=9.0 Hz), 4.02 (2H, m), 2.35 (2H, m), 2.15 (1H, m), 1.65–1.86 (4H, m), 1.56 (1H, m), 1.02–1.38 (66H, m), 0.79 (6H, t, J=6.7 Hz).

$^{13}$C-NMR spectrum (125 MHz, deuteropyridine+1% of heavy water): δ (ppm) 173.6 (s), 100.7 (d), 100.6 (d), 76.4 (d), 75.5 (d), 73.4 (d), 72.6 (d), 72.4 (d), 72.4 (d), 72.0 (d), 71.7 (d), 71.1 (d), 70.8 (d), 68.0 (t), 67.5 (t), 62.7 (t), 51.5 (d), 36.8 (t), 34.3 (t), 32.2 (t), 30.4 (t), 30.2 (t), 30.1 (t), 30.1 (t), 29.9 (t), 29.8 (t), 29.8 (t), 29.6 (t), 26.5 (t), 26.4 (t), 23.0 (t), 14.3 (q).

Synthesis of Compound 32

The mixture of Compound 29 (102.5 mg, 0.12 mmol), stannous chloride (52.0 mg, 0.27 mmol), silver perchlorate (56.8 mg, 0.27 mmol) and Molecular Sieves-4A (500 mg) was suspended in tetrahydrofuran (2 ml), and the suspension was stirred at room temperature for 1 hour. After the suspension was cooled to −10° C., a solution of α-6-O-(tetra-O-benzylgalactopyranosyl)-2,3,4-tri-O-benzylglucopyranosyl fluoride (227.5 mg, 0.23 mM) in tetrahydrofuran (2 ml) was added to the suspension. After the temperature was slowly raised up to room temperature, the reaction mixture was stirred for 16 hours, filtered through Celite, concentrated to dryness, and purified by column chromatography on silica gel (ethyl acetate:n-hexane=3:17) to give Compound 32 (141) in an amount of 67.5 mg (31.6%).

$^1$H-NMR (500 MHz/$CDCl_3$): δ (ppm) 7.14–7.38 (45H, m), 6.05 (1H, d, J=8.6 Hz), 4.33–4.91 (20H, m), 4.22 (1H, m), 4.03 (3H, m), 3.90–3.97 (6H, m), 3.85 (1H, dd, J=2.5, 6.8 Hz), 3.80 (1H, d, J=5.4, 8.5 Hz), 3.70 (1H, dd, J=4.8, 9.7 Hz), 3.60 (1H, dd, J=8.6, 8.8 Hz), 3.45–3.55 (3H, m), 1.95 (1H, m), 1.87 (1H, m), 1.62 (2H, m), 1.48 (2H, m), 1.10–1.34 (68H, m), 0.88 (6H, t, J=6.7 Hz).

Synthesis of Compound 33

To a solution of Compound 32 (61.5 mg) in ethyl acetate (2 ml) was added palladium black (60 mg), and the mixture was stirred under hydrogen stream at room temperature for 16 hours. The reaction mixture was filtered through celite and purified by column chromatography on silica gel (chloroform:methanol:water=9:1:0.1) to give Compound 33 in an amount of 20.8 mg (60.7%).

Optical rotation: $[\alpha]_D^{23}$=+75.0° (pyridine, c=1.07).

High resolution FABMS analysis: 1018.7703 |(M-H)⁻, theoretical value 1018.7776, based on $C_{56}H_{108}NO_{14}$ with an error of 7.3 mMU|.

Infrared absorption spectrum: (KBr, cm$^{-1}$) 3400, 2950, 2870, 1645, 1535, 1475, 1080.

Melting point: 127.0°–131.0° C.

$^1$H-NMR spectrum (500 MHz, deuteropyridine+1% of heavy water): δ (ppm) 8.52 (1H, d, J=8.6 Hz), 5.48 (2H, m), 5.19 (1H, m), 4.69 (1H, dd, J=4.8, 10.3 Hz), 4.66 (2H, m), 4.54–4.63 (4H, m), 4.46–4.55 (2H, m), 4.36–4.46 (3H, m), 4.22–4.36 (4H, m), 2.46 (2H, m), 2.24 (1H, m), 1.90 (2H, m), 1.81 (2H, m), 1.67 (1H, m), 1.12–1.45 (66H, m), 0.86 (6H, t, J=6.7 Hz).

$^{13}$C-NMR spectrum (125 MHz, deuteropyridine+1% of heavy water): δ (ppm) 173.7 (s), 101.0 (d), 100.9 (d), 76.3 (d), 72.7 (d), 72.6 (d), 71.7 (d), 71.4 (d), 71.0 (d), 70.7 (d), 70.7 (d), 70.5 (d), 70.3 (d), 68.1 (t), 67.8 (t), 62.5 (t), 51.6 (d), 36.9 (t), 34.3 (t), 32.2 (t), 30.5 (t), 30.2 (t), 30.1 (t), 30.1 (t), 30.0 (t), 29.9 (t), 29.8 (t), 29.6 (t), 26.5 (t), 26.5 (t), 23.0 (t), 14.3 (q).

Synthesis of Compound 34

The mixture of Compound 29 (350.6 mg, 0.40 mmol), stannous chloride (189.2 mg, 1.00 mmol), silver perchlorate (206.9 mg, 1.00 mmol) and Molecular Sieves-4A (2.5 g) was suspended in tetrahydrofuran (3 ml), and the suspension was stirred at room temperature for 1 hour. After the suspension was cooled to −10° C., a solution of α-4-O-(tetra-O-benzylglucopyranosyl)-2,3,6-tri-O-benzylglucopyranosyl fluoride (778.4 mg, 0.80 mM) in tetrahydrofuran (2 ml) was added to the suspension. After the temperature was slowly raised up to room temperature, the reaction mixture was stirred for 16 hours, filtered through celite, concentrated to dryness, and purified by column chromatography on silica gel (ethyl acetate:n-hexane=1:9) to give Compound 34 (168) in an amount of 95.05 mg (13.0%).

$^1$H-NMR (500 MHz/CDCl$_3$): δ (ppm) 7.14–7.41 (45H, m), 6.11 (1H, d, J=8.6 Hz), 5.73 (1H, d, J=3.7 Hz), 5.05 (1H, d, J=11.6 Hz), 4.43–4.94 (17H, m), 4.33 (1H, d, J=11.6 Hz), 4.26 (1H, m), 4.12 (1H, t, J=9.2 Hz), 4.07 (1H, t, J=9.2 Hz), 3.98 (2H, m), 3.95 (1H, m), 3.92 (1H, m), 3.87 (1H, dd, J=3.1, 7.3 Hz), 3.82 (1H, dd, J=4.3, 11.0 Hz), 3.76 (1H, m), 3.70 (1H, m), 3.66 (1H, m), 3.65 (1H, m), 3.52–3.62 (3H, m), 3.44 (1H, bd, J=10.4 Hz), 2.08 (1H, m), 2.03 (1H, m), 1.74 (1H, m), 1.68 (1H, m), 1.59 (2H, m), 1.10–1.45 (68H, m), 0.94 (6H, t, J=6.7 Hz).

Synthesis of Compound 35

To a solution of Compound 34 (95.0 mg) in ethyl acetate (3 ml) was added palladium black (42 mg), and the mixture was stirred under hydrogen atmosphere at room temperature for 16 hours. The reaction mixture was filtered through Celite to give Compound 35 in an amount of 50.7 mg (95.8%).

Optical rotation: $|\alpha|_D^{23}$=+60.1° (pyridine, c=0.6).

High resolution FABMS analysis: 1018.7719 [(M-H)$^-$, theoretical value 1018.7776, based on C$_{56}$H$_{108}$NO$_{14}$ with an error of 5.7 mMU].

Infrared absorption spectrum: (KBr, cm$^{-1}$) 3400, 2950, 2870, 1645, 1535, 1475, 1080.

Melting point: 145.0°–148.5° C.

$^1$H-NMR spectrum (500 MHz, deuteropyridine+1% of heavy water): δ (ppm) 8.49 (1H, d, J=8.6 Hz), 5.85 (1H,d, J=3.1 Hz), 5.48 (1H, d, J=3.7 Hz), 5.20 (1H, m), 4.44–4.65 (5H, m), 4.40 (1H, m), 4.22–4.36 (6H, m), 4.08–4.22 (3H, m), 4.04 (1H, dd, J=3.1, 9.8 Hz), 2.41 (2H, t, J=7.3 Hz), 2.25 (1H, m), 1.70–1.95 (4H, m), 1.64 (1H, m), 1.05–1.48 (66H, m), 0.86 (6H, t, J=6.1 Hz).

$^{13}$C-NMR spectrum (125 MHz, deuteropyridine+1% of heavy water): δ (ppm) 173.3 (s), 103.3 (d), 100.7 (d), 81.7 (d), 76.6 (d), 75.5 (d), 75.3 (d), 74.8 (d), 74.6 (d), 73.0 (d), 72.9 (d), 72.4 (d), 71.9 (d), 68.3 (t), 62.7 (t), 61.7 (t), 51.2 (d), 36.8 (t), 34.4 (t), 32.2 (t), 30.5 (t), 30.2 (t), 30.1 (t), 30.1 (t), 30.0 (t), 29.9 (t), 29.9 (t), 29.8 (t), 29.7 (t), 26.5 (t), 26.4 (t), 23.0 (t), 14.4 (q).

EXPERIMENTAL EXAMPLE 4: ANTI-TUMOR ACTIVITY OF THE COMPOUND OF THE PRESENT INVENTION i) Anti-tumor effect of the compound of the present invention on mice subcutaneously inoculated with P388 mouse leukemia cells.

Experiment was performed with CDF$_1$ female mice (6 weeks) purchased from NIPPON SLC K.K., which were divided into groups consisting of 5 animals. P388 mouse leukemia cells were implanted subcutaneously into back of mice in a level of 1×10$^6$ cells/mouse (implantation day: day 0), and a vehicle (10 ml/kg) or a compound (0.1 mg/kg) dissolved in a vehicle was administered intravenously on days 1, 5 and 9 after implantation in order to observe the survival days of the animals. In this connection, lentinan and picibanil were administered intravenously on days 1, 3, 5, 7 and 9 after implantation, and sizofilan was administered subcutaneously on days 1 through 9. Statistical analysis was performed according to the Mann-Whiteney test. The results are shown in Table 1.

TABLE 1

Life-span-prolonging effect on P388 s. c. system

| Compound | Dose (mg/kg) | Survival days ave. ± s. d. | T/C (%) |
|---|---|---|---|
| Vehicle | — | 12.8 ± 0.4 | 100 |
| 1 | 0.1 | 15.3 ± 0.8** | 120 |
| 2 | 0.1 | 15.8 ± 0.5** | 123 |
| 3 | 0.1 | 15.0 ± 0** | 117 |
| 4 | 0.1 | 15.2 ± 0.5** | 119 |
| 5 | 0.1 | 15.2 ± 1.1** | 119 |
| 6 | 0.1 | 15.8 ± 1.1** | 123 |
| 7 | 0.1 | 15.8 ± 0.9** | 123 |
| 8 | 0.1 | 16.0 ± 0.7** | 125 |
| 9 | 0.1 | 16.4 ± 1.8** | 128 |
| 10 | 0.1 | 13.8 ± 0.4** | 108 |
| 11 | 0.1 | 13.4 ± 0.5** | 105 |
| 12 | 0.1 | 13.8 ± 0.8** | 108 |
| 13 | 0.1 | 14.6 ± 0.5** | 114 |
| 14 | 0.1 | 13.8 ± 0.4** | 108 |
| 15 | 0.1 | 14.0 ± 0** | 109 |
| 16 | 0.1 | 14.8 ± 0.8** | 116 |
| 17 | 0.1 | 14.8 ± 0.8** | 116 |
| 31 | 0.1 | 14.6 ± 0.5** | 114 |
| 33 | 0.1 | 15.0 ± 0.7** | 117 |
| 35 | 0.1 | 14.8 ± 1.3** | 116 |
| b | 0.1 | 15.6 ± 0.5** | 122 |
| Lentinan | 1 | 13.6 ± 0.5 | 106 |
| Lentinan | 2 | 13.2 ± 0.8 | 103 |
| Sizofilan | 1 | 13.2 ± 0.8 | 103 |
| Sizofilan | 10 | 12.6 ± 0.5 | 98 |
| Picibanil | 1KE/mouse | 13.6 ± 0.9 | 106 |

*: $p < 0.05$, Mann-Whitney tst;
**: $p < 0.01$.

As shown in Table 1, it has become clear that all of the compounds except Compounds 11 and 12 exhibit significant life-span-prolonging effects (anti-tumor effects) on mice subcutaneously inoculated with P388 mouse leukemia cells. On the other hand, neither of lentinan, Sizofilan or picibanil exhibited life-span-prolonging effects. Thus, all of the compounds according to the present invention except Compounds 11 and 12 exhibited an anti-tumor effect stronger than currently available lentinan, Sizofilan or picibanil. Furthermore, it was also found that when (2S,3S,4R)-1-(α-D-galactopyranosyloxy)-2-hexacosanoylamino-3,4-octadecanediol (Compound b) comprising a monosaccharide as the sugar portion was synthesized and examined its anti-tumor effect. Compounds 31, 33 and 35 exhibited intensive anti-tumor effects almost in the same level as that of Compound b.

ii) Anti-tumor effect of the compound according to the present invention on mice subcutaneously inoculated with B16 mouse melanoma cells.

Experiment was performed with $BDF_1$ female mice (6 weeks) purchased from NIPPON SLC K.K., which were divided into groups consisting of 6 animals. B16 mouse melanoma cells were implanted subcutaneously into back of mice in a level of $1 \times 10^6$ cells/mouse (implantation day: day 0), and each sample at a dose of 0.1 mg/kg was administered intravenously into tail vein on days 1, 5 and 9 after implantation. The subcutaneous tumor volumes |(length×width× height)/2| were measured on days 8, 12, 16 and 20 after implantation to determine the tumor growth inhibiting rate (TGIR) of each sample. TGIR was calculated from the following formula:

TGIR(%)=(1-T/C)×100 wherein C: tumor volume in the control group, and

T: tumor volume in the sample adminitered groups.

Maximum TGIR during the test for 20 days is shown in the table below. In this connection, Compounds 1–6 and 7–9 were tested in the same time, respectively.

| Compound | TGIR (%) |
|---|---|
| 1 | 71 4 |
| 2 | 82.6 |
| 3 | 66.8 |
| 4 | 84.0 |
| 5 | 86.8 |
| 6 | 91.2 |
| 7 | 78.1 |
| 8 | 78.4 |
| 9 | 74.8 |

All of the compounds exhibited intensive tumor growth inhibitory effects.

EXPERIMENTAL EXAMPLE 5: BONE MARROW CELL-PROLIFERATION-PROMOTING EFFECT OF THE PRESENT COMPOUND

In vitro mouse bone marrow cell-proliferation-promoting effect of the present compound Experiment was performed with $BDF_1$ female mice (6 weeks old) purchased from NIPPON SLC K.K. Bone marrow cells were removed from the femoral bone of mice by the conventional manner, floated on 10% FCS RPMI 1640, layered over Lympholite M, and centrifuged to give a monocyte fraction. $1 \times 10^6$ cells/ml of the monocyte fraction was suspended in 10% FCS RPMI 1640. The cell suspension (100 μl/well) and a vehicle or sample (10 μl/well) which was prepared so as to have a final level shown in Table 2 were added into a wells of round-bottomed 96 well plate, and cultured under the condition of 5% $CO_2$ at 37° C. for 4 days. 0.5 μCi/well of $^3$H-thymidine ($^3$H-TdR) was added. After 6 hours, the cells were harvested, and the amount of $^3$H-TdR uptaken into nucleus was measured by a liquid scintillation counter. The ratio of the uptake of $^3$H-TdR in the sample group to that in the vehicle group was calculated and used as the activation rate for promoting in vitro mouse bone marrow cell growth.

The results are shown in Table 2.

TABLE 2

In vitro bone marrow cell-proliferation-promoting effects of the present compounds

| Compound | Uptake of $^3$H-TdR (% of control) Concentration (μg/ml) | |
|---|---|---|
| | $10^{-1}$ | $10^{-2}$ |
| 1 | 211 | 133 |
| 2 | 268 | 276 |
| 3 | 314 | 138 |
| 4 | 512 | 163 |
| 5 | 330 | 283 |
| 6 | 431 | 142 |
| 7 | 451 | 478 |
| 8 | 240 | 167 |
| 9 | 286 | 91 |
| 10 | 286 | 147 |
| 11 | 410 | 281 |
| 12 | 381 | 378 |
| 13 | 546 | 395 |
| 14 | 838 | 659 |
| 15 | 501 | 291 |
| 16 | 325 | 296 |
| 17 | 592 | 1098 |
| 31 | 296 | 594 |
| 33 | 214 | 763 |
| 35 | 223 | 148 |
| b | 381 | 438 |

As shown in Table 2, all of the compounds in a of at least 0.1 μg/ml exhibited an intensive $^3$H-TdR-promoting effect. It was thus indicated that all of the compounds of the present invention have an intensive bone marrow cell-proliferation-promoting activity.

EXPERIMENTAL EXAMPLE 6: IMMUNOSTIMULATING EFFECTS OF THE PRESENT COMPOUNDS i) In vitro mouse splenic lymphocyte growth promoting effects of the present compounds Experiment was performed with $BDF_1$ female mice (6 weeks old) purchased from NIPPON SLC K.K. Spleens were removed from mice, and spleen cells were brayed with slide glasses and hemolized with $NH_4Cl$. $2 \times 10^6$ cells/ml of the spleen cells which had been hemolized were suspended in 10% FCS RPMI 1640. The cell suspension (100 μl/well) and a vehicle or sample (10 μl/well) which was prepared so as to have a final level shown in Table 3 were added into wells of a round-bottomed 96 well plate, and cultured under the condition of 5% $CO_2$ at 37° C. for 2 days. 0.5 μCi/well of $^3$H-thymidine ($^3$H-TdR) was added. After 6 hours, the cells were harvested, and the amount of $^3$H-TdR uptaken into nucleus was measured by a liquid scintillation counter. The ratio (%) of the uptake of $^3$H-TdR in the sample group to that in the vehicle group was calculated and used as the in vitro mouse splenic lymphocyte-proliferation-stimulating rate.

The results are shown in Table 3.

TABLE 3

In vitro mouse splenic lymphocyte-proliferation-stimulating effects of the present compounds

| Compound | Uptake of $^3$H-TdR (% of control) Concentration (μg/ml) | | | |
|---|---|---|---|---|
|  | $10^0$ | $10^{-1}$ | $10^{-2}$ | $10^{-3}$ |
| 1  | 843  | 738  | 332  | 184  |
| 2  | 890  | 735  | 508  | 270  |
| 3  | 815  | 704  | 397  | 258  |
| 4  | 792  | 692  | 395  | 325  |
| 5  | 889  | 764  | 612  | 592  |
| 6  | 883  | 979  | 649  | 543  |
| 7  | 927  | 1082 | 705  | 593  |
| 8  | 997  | 1318 | 1321 | 609  |
| 9  | 902  | 924  | 1305 | 513  |
| 10 | 509  | 375  | 277  | 102  |
| 11 | 646  | 1012 | 858  | 116  |
| 12 | 509  | 982  | 772  | 113  |
| 13 | 788  | 1473 | 1769 | 227  |
| 14 | 640  | 1116 | 1725 | 252  |
| 15 | 845  | 1893 | 1417 | 394  |
| 16 | 740  | 1365 | 1336 | 702  |
| 17 | 781  | 1804 | 1747 | 767  |
| 31 | 615  | 1347 | 1135 | 744  |
| 33 | 954  | 1810 | 1811 | 1514 |
| 35 | 431  | 874  | 803  | 538  |

As shown in Table 3, all of the compounds according to the present invention in a concentration of 10 ng/ml - 1 μg/ml exhibited an intensive $^3$H-TdR-uptake-promoting effect. It was found that since the assay system is the one for examining the blast formation of lymphocytes by mitogen, all of the compounds according to the present invention have an intensive ability of forming lymphocytic blast (Junichi Yada & Michio Fujiwara, "New Method for searching for functions of lymphocyte", Chugai Igaku-sha (1990)). In addition, as shown in the paragraph ii), it has been confirmed that all of the compounds of the present invention exhibit an intensive MLR (mixed lymphocyte culture reaction) activity enhancing effect.

ii) Mixed lymphocyte culture reaction (MLR) of the compounds of the present invention Spleen cells were prepared from C57BL/6 mice and treated with 50 μg/ml of mitomycin C for 30 minutes. The treated cells were used as stimulator cells, and the spleen cells of BALB/C mice as responder cells. $2\times10^6$ cells/ml of the both spleen cells were suspended in 10% FCS RPMI1640 as a culture medium. The above-described cells (50 μl/well) and a sample (10 μl/well) were added into wells of a round-bottomed 96 well plate, and cultured under the condition of 5% $CO_2$ at 37° C. for 42 hours. 0.5 μCi/well of $^3$H-thymidine ($^3$H-TdR) was added. After 8 hours, the cells were harvested, and the amount of uptaken $^3$H-TdR was measured by a liquid scintillation counter to calculate the ratio (%) of the uptake of $^3$H-TdR in the sample group to that in the vehicle group as the MLR activating rate.

The results are shown in the following table.

| Compound | MLR activating rate (%) | |
|---|---|---|
|  | $1 \times 10^0$ | $1 \times 10^{-1}$ (μg/ml) |
| 1 | 222 | 142 |
| 2 | 213 | 158 |
| 3 | 210 | 138 |
| 4 | 209 | 163 |

-continued

| Compound | MLR activating rate (%) | |
|---|---|---|
|  | $1 \times 10^0$ | $1 \times 10^{-1}$ (μg/ml) |
| 5  | 189 | 176 |
| 6  | 228 | 194 |
| 7  | 234 | 195 |
| 8  | 286 | 232 |
| 9  | 247 | 205 |
| 10 | 174 | 132 |
| 11 | 225 | 258 |
| 12 | 203 | 187 |
| 13 | 276 | 248 |
| 14 | 261 | 232 |
| 15 | 295 | 253 |
| 16 | 274 | 262 |
| 17 | 283 | 242 |
| 31 | 206 | 196 |
| 33 | 302 | 251 |
| 35 | 165 | 133 |

All of the compounds exhibit an intensive MLR activating effect.

EXPERIMENTAL EXAMPLE 7: RADIOPROTECTIVE EFFECTS OF THE PRESENT COMPOUNDS

Life-span-prolonging effects of the present compounds on lethally irradiated mice.

Experiment was performed with $BDF_1$ female mice (6 weeks old) purchased from NIPPON SLC K.K., which were divided into groups consisting of 10 animals. Mice were irradiated generally with 9 Gy of X-ray with an X-ray generating apparatus, Hitachi, MBR-1520R (radiation day: day 0). Samples at a dose of 0.1 mg/kg were administered into tail vein on days 0, 4 and 8 in order to observe the mortality of the animals for 40 days.

The results are shown in the following table. In the table, two experiments are separated by the broken line.

| Compound | Number of surviving mice | | | | | | |
|---|---|---|---|---|---|---|---|
|  | 10 | 15 | 20 | 25 | 30 | 35 | 40 (days) |
| Control    | 10 | 5  | 2  | 1 | 0 | 0 | 0 |
| Compound 1 | 10 | 9  | 7  | 6 | 6 | 6 | 6 |
| Compound 2 | 10 | 10 | 10 | 9 | 9 | 9 | 9 |
| Compound 3 | 10 | 6  | 5  | 5 | 5 | 5 | 5 |
| Compound 4 | 10 | 8  | 8  | 6 | 5 | 5 | 5 |
| Compound 5 | 10 | 8  | 7  | 7 | 7 | 7 | 7 |
| Compound 6 | 10 | 10 | 8  | 8 | 8 | 8 | 8 |
| Control    | 9  | 7  | 0  | 0 | 0 | 0 | 0 |
| Compound 7 | 10 | 8  | 6  | 3 | 3 | 3 | 3 |
| Compound 8 | 8  | 4  | 3  | 2 | 2 | 2 | 2 |
| Compound 9 | 10 | 8  | 5  | 3 | 3 | 3 | 3 |

All of the compounds exhibited an intensive life-spanprolonging effect on lethally irradiated mice.

EXPERIMENTAL EXAMPLE 8: SOLUBILITY IN WATER OF THE PRESENT COMPOUNDS

Compounds a and b comprising a monosaccharide as a constituent sugar which are disclosed in WO 93/05055 were synthesized as above. A 1 mg of each of the present compounds 4, 31 and 33 and Compound a and b was dissolved in 1 ml of an aqueous Polysorbate 20 solution in a variety of concentrations in order to observe visually the property. The results are shown in Table 4

TABLE 4

Comparison of solubilities in water

| Concentration of Polysorbate 20 | Compound a | Compound b | Compound 4 | Compound 31 | Compound 33 |
|---|---|---|---|---|---|
| 10% | ○ | ○ | ○ | ○ | ○ |
| 5% | ○ | X | ○ | ○ | ○ |
| 2.5% | X | X | ○ | ○ | ○ |
| 1% | X | X | ○ | ○ | ○ |
| 0.1% | X | X | ○ | ○ | ○ |
| 0% | X | X | X | X | X |

○: soluble;
X: insoluble (turbid).

It has been found out from Table 4 that if Compounds 4, 31 or 33 is used as the typical compound of the present invention, it is possible to decrease the amount of Polysorbate 20 which is required for dissolving these compounds in water to a level of 1/100 of the amount of Polysorbate 20 required for dissolving Compound b which comprises a monosaccharide as the constituent sugar and exhibits a similar anti-tumor activity to that of Compounds 4, 31 or 33.

EXPERIMENTAL EXAMPLE 9: INFLUENCE OF POLYSORBATE ON IMMUNOSTIMULATING EFFECT

A sample of a solution of 1 mg of Compound 33 prepared in Experimental Example 8 in 1 ml of 10% or 0.1% Polysorbate 20, a sample of a solution of 1 mg of Compound b in 1 ml of 10% Polysorbate 20, or 10% and 0.1% Polysorbate 20, were prepared by subjecting to aseptic filtration followed by sequential 10 time dilution with PBS as shown in Table 5 in order to carry out the experiment described in Experimental Example 6.

In this connection, 1 mg of Compound b was insoluble in 0.1% Polysorbate, and thus no experiment was conducted.

TABLE 5

| Compound/ dilution | $^3$H-TdR uptake (cpm) | | | |
|---|---|---|---|---|
| | $10^2$ | $10^3$ | $10^4$ | $10^5$ |
| 10% PS20 | 203 | 890 | 1868 | 2186 |
| b (10% PS20) | 201 | 18300 | 24439 | 25555 |
| 33 (10% PS20) | 119 | 18447 | 24671 | 21677 |
| 0.1% PS20 | 1774 | 1794 | 1871 | 1910 |
| 33 (0.1% PS20) | 24213 | 23332 | 26249 | 23653 |

Means of 3 wells were shown.

As shown in Table 5, the amount of $^3$H-TdR uptaken into mouse splenic lymphocytes was suppressed apparently by the addition of 0.1% and 0.01% of Polysorbate 20 as compared with the addition of 0.001% or less of Polysorbate 20. Furthermore, it has been also proved that $^3$H-TdR uptake is suppressed in the concentrations of Compound 33 and b of 10 µg/ml (0.1% Polysorbate 20) and 1 µg/ml (0.01% Polysorbate 20) as compared with that in the concentration of 0.1 µg/ml (0.001% Polysorbate 20).

It has been proved from these results that a high concentration (0.01% or more) of Polysorbate 20 suppresses the proliferation of mouse splenic lymphocytes and the immunostimulating effect of the compounds of the present invention as well.

Thus, when a solution sample of Compound 33 was prepared with Polysorbate 20 of which amount had been decreased to a proportion of 1/100 to perform the same experiment as above, Compound 33 exhibited an intensive $^3$H-TdR-uptake-stimulating effect even in a concentration of 10 µg/ml (0.001% Polysorbate 20).

It has been proved from these results that the immunostimulating effect of the present compounds can be recovered by decreasing the amount of Polysorbate 20 used for dissolving the compounds.

The results of Experimental Examples 4–8 can be described briefly as follows.

It has been proved that the compounds according to the present invention except Compounds 11 and 12 exhibit an intensive anti-tumor effect as compared with that of lentinan, Sizofilan and picibanil as well as an intensive anti-tumor effect almost in the same level as that of Compound b which is a sphingoglycolipid included in the formulae described in Japanese Patent Laid-Open Publication No. 9193/1993 and WO 93/05055 (Table 1).

It has been also proved that the compounds according to the present invention exhibit an intensive bone marrow cell-proliferation-promoting effect (Table 2) and an intensive immunostimulating effect (Table 3 and 5), and these effects are almost in the same level as that of the sphingoglycolipid as Compound b.

In addition, it has been proved the amount of a dissolving aid such as Polysorbate which is required for dissolving the compounds according to the present invention in water may be in the level of 1/100 as compared with that of the dissolving aid required for dissolving Compounds a and b which are the sphingoglycolipids included in the formulae described in Japanese Patent Laid-Open Publication No. 9193/1993 and WO 93/05055.

Finally, it has been proved that the suppressive effects of Polysorbate 20 at a high concentration on the proliferation of cells and the immunostimulating activity which can be considered as the side effects of Polysorbate 20 at a high concentration can be solved by decreasing the amount of Polysorbate 20.

It is a present situation that the compounds having a low solubility in water are very difficult to make application to injection due to the side effects of the dissolving aid as desribed above. Such compounds with a decreased amount of the dissolving aid have a further defect of the limited administration routes due to the regulation that any suspensions should not be administered intravascularly or intraspinally (see Revised Version of Japanese PHarmacopoeia, Commentary (1991), pp. A119–A136).

As described above, it has been proved that the compounds of the present invention is the compound which exhibits biological activities almost in the same level as those of a sphingoglycolipid having a monosaccharide as a sugar constituent such as Compounds a and b and can avoid the problem caused in the such cases that the sphingoglycolipid is intended to be applied as injections.

That is to say, the compound according to the present invention is useful in the point that the side effects of the dissolving aid can be reduced on its application to injections and the administration routes are not limited as compared with the sphingoglycolipids described in Japanese Patent Laid-Open Publication No. 9193/1993 and WO 93/05055.

EXPERIMENTAL EXAMPLE 10: PHARMACEUTICAL PREPARATION EXAMPLES

Example 1

| Injection | |
|---|---|
| The compound of the present invention | 1 mg |
| Polysorbate | 1 mg |
| Distilled water for injection | q.s. |
| Total | 1 ml |

According to the above described formulation, the compound is dissolved in distilled water for injection, filtered aseptically and filled in a vial or ampoule to give an injection.

Example 2

| Tablet | |
|---|---|
| (1) The compound of the present invention | 1 mg |
| (2) Lactose | 80 mg |
| (3) Corn starch | 30 mg |
| (4) Hydroxypropyl cellulose | 3 mg |
| (5) Magnesium stearate | 1 mg |
| Total | 115 mg |

According to the above described formulation, compounds (1)–(5) were blended and granulated into granulations for punching. Compound (5) was added to the granulations to form a homogeneous powder, which is subjected to compression molding on a punching machine to form tablets.

Industrial Applicability

The compound of the present invention is a novel sphingoglycolipid having an intensive anti-tumor activity, bone marrow cell-proliferation-promoting activity and immunostimulating effect, and is useful as an anti-tumor agent, a bone marrow cell-proliferation-promoting agent and an immunostimulating agent.

What is claimed is:

1. A sphingoglycolipid represented by the formula (I):

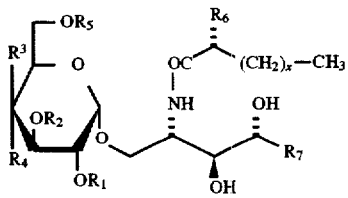

wherein $R_1$, represents H or

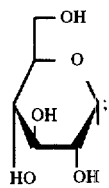

$R_2$ represents H.

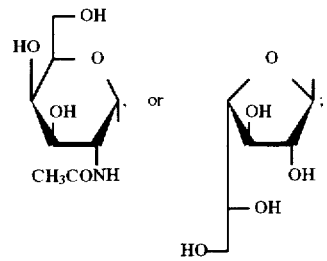

$R_3$ and $R_6$ represent H or OH, respectively;
$R_4$ represents H., OH, or

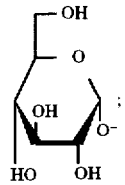

$R_5$ represents H or

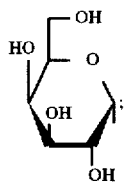

X denotes an integer from 19 to 23; and
$R_7$ represents any one of the following groups (a)–(g):
(a) —$(CH_2)_{11}$—$CH_3$,
(b) —$(CH_2)_{12}$—$CH_3$,
(c) —$(CH_2)_{13}$—$CH_3$,
(d) —$(CH_2)_9$—$CH(CH_3)_2$,
(e) —$(CH_2)_{10}$—$CH(CH_3)_2$,
(f) —$(CH_2)_{11}$—$CH(CH_3)_2$,
(g) —$(CH_2)_{11}$—$CH(CH_3)$-$C_2H_5$,
wherein at least one of $R_1$, $R_2$, $R_4$ and $R_5$ is a glycosyl moiety.

2. A sphingoglycolipid represented by the formula (II):

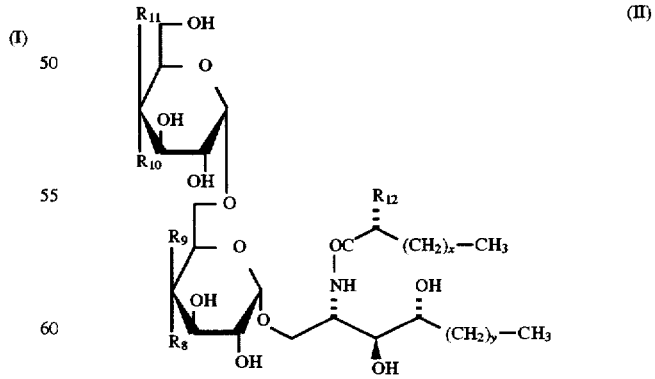

wherein $R_8$ represents H or OH and if $R_8$ represents OH, $R_9$ represents H, and if $R_8$ represents H, $R_9$ represents OH;
$R_{10}$ represents H or OH and if $R_{10}$ represents OH, $R_{11}$ represents H, and if $R_{10}$ represents H, $R_{11}$ represents OH;

$R_{12}$ represents H or OH;

X denotes an integer from 19 to 23; and

Y denotes an integer from 11 to 13.

3. A sphingoglycolipid represented by the formula (III):

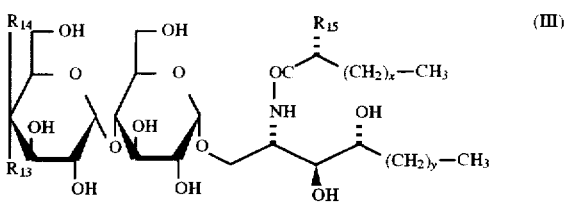

wherein $R_{13}$ represents OH or H and if $R_{13}$ represents OH, $R_{14}$ represents H, and if $R_{13}$ represents H, $R_{14}$ represents OH;

$R_{15}$ represents H or OH;

X denotes an integer from 19 to 23; and

Y denotes an integer from 11 to 13.

4. A sphingoglycolipid according to claim 1, which is selected from the group consisting of the following compounds:

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-1,3,4-hexadecanetriol;

O-(N-acetyl-2-amino-2-deoxy-α-D-galactopyranosyl)-(1→3)-O-|α-D-glucopyranosyl-(1 →2)|-O-α-D-galactopyranosyl-(1→1)-(2S,3S,4R)-2-amino-N-|(R)-2-hydroxytetracosanoyl|-1,3,4-heptadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-16-methyl-1,3,4-heptadedanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxytetracosanoyl|-1,3,4-octadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R) 2-hydroxypentacosanoyl|-16-methyl-1,3,4-heptadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxypentacosanoyl|-1,3,4-octadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxyhexacosanoyl|-16-methyl-1,3,4-heptadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxyhexacosanoyl|-1,3,4-octadecanetriol;

O-(N-acetyl-2-amino-2-deoxy-α-D-galactopyranosyl)-(1→3)-O-|α-D-glucopyranosyl-(1→2)|-O-α-D-galactopyranosyl-(1→1)-(2S,3S,4R)-2-amino-N-|(R)-2-hydroxyhexacosanoyl|-16-methyl-1,3,4-octadecanetriol;

O-β-D-galactofuranosyl-(1→3)-O-α-D-galactopyranosyl-(1→1)-(2S,3S,4R)-2-amino-N-|(R)-2-hydroxydocosanoyl|-1,3,4-hexadecanetriol;

O-β-D-galactofuranosyl-(1→3)-O-α-D-galactopyranosyl-(1→1)-(2S,3S,4R)-2-amino-N-|(R)-2-hydroxytricosanoyl|-1,3,4-hexadecanetriol;

O-β-D-galactofuranosyl-(1→3)-O-α-D-galactopyranosyl-(1→1)-(2S,3S,4R)-2-amino-N-|(R)-2-hydroxytetracosanoyl|-1,3,4-hexadecanetriol;

O-β-D-galactofuranosyl-(1→3)-O-α-D-galactopyranosyl-(1→1)-(2S,3S,4R)-2-amino-N-|(R)-2-hydroxytetracosanoyl|-15-methyl-1,3,4-hexadecanetriol;

O-β-D-galactofuranosyl-(1→3)-O-α-D-galactopyranosyl-(1→1)-(2S,3S,4R)-2-amino-N-|(R)-2-hydroxytetracosanoyl|-1,3,4-heptadecanetriol;

O-β-D-galactofuranosyl-(1→3)-O-α-D-galactopyranosyl-(1→1)-(2S,3S,4R)-2-amino-N-|(R)-2-hydroxytetracosanoyl|-16-methyl-1,3,4-heptadecanetriol;

O-β-D-galactofuranosyl-(1→3)-O-α-D-galactopyranosyl-(1→1)-(2S,3S,4R)-2-amino-N-|(R)-2-hydroxytetracosanoyl|-1,3,4-octadecanetriol;

O-β-D-galactofuranosyl-(1→3)-O-α-D-galactopyranosyl-(1→1)-(2S,3S,4R)-2-amino-N-|(R)-2-hydroxytetracosanoyl|-17-methyl-1,3,4-octadecanetriol;

O-α-D-galactopyranosyl-(1→6)-O-α-D-glucopyranosyl-(1→1)-(2S,3S,4R)-2-amino-N-hexacosanoyl-1,3,4-octadecanetriol;

O-α-D-galactopyranosyl-(1→6)-O-α-D-galactopyranosyl-(1→1)-(2S,3S,4R)-2-amino-N-hexacosanoyl-1,3,4-octadecanetriol; and O-α-D-glucopyranosyl-(1→4)-O-α-D-glucopyranosyl-(1→1)-(2S,3S,4R)-2-amino-N-hexacosanoyl-1,3,4-octadecanetriol.

5. A sphingoglycolipid according to claim 4, which is selected from the group consisting of the following compounds:

O-α-D-galactopyranosyl-(1→6)-O-α-D-glucopyranosyl-(1→1)-(2S,3S,4R)-2-amino-N-hexacosanoyl-1,3,4-octadecanetriol;

O-α-D-galactopyranosyl-(1→6)-O-α-D-galactopyranosyl-(1→1)-(2S,3S,4R)-2-amino-N-hexacosanoyl-1,3,4-octadecanetriol; and O-α-D-glucopyranosyl-(1→4)-O-α-D-glucopyranosyl-(1→1)-(2S,3S,4R)-2-amino-N-hexacosanoyl-1,3,4-octadecanetriol.

6. A pharmaceutical composition comprising the sphingoglycolipid described in claim 1 as an effective ingredient and a pharmaceutically acceptable carrier or diluent.

7. A pharmaceutical composition comprising the sphingoglycolipid described in claim 2 as an effective ingredient and a pharmaceutically acceptable carrier or diluent.

8. A pharmaceutical composition comprising the sphingoglycolipid described in claim 3 as an effective ingredient and a pharmaceutically acceptable carrier or diluent.

9. A pharmaceutical composition comprising the sphingoglycolipid described in claim 4 as an effective ingredient and a pharmaceutically acceptable carrier or diluent.

10. A pharmaceutical composition comprising the sphingoglycolipid described in claim 5 as an effective ingredient and a pharmaceutically acceptable carrier or diluent.

11. A process for inhibiting tumor growth wherein an effective amount of the sphingoglycolipid described in claim 1 is administered to a patient who needs inhibition of tumor growth.

12. A process for promoting proliferation of bone marrow cells, wherein an effective amount of the sphingoglycolipid described in claim 1 is administered to a patient who needs promotion of the proliferation of bone marrow cells.

13. A process for stimulation of the immune system, wherein an effective amount of the sphingoglycolipid described in claim 1 is administered to a patient who needs stimulation of the immune system.

* * * * *